United States Patent [19]
D'Angelo et al.

[11] Patent Number: 5,405,614
[45] Date of Patent: Apr. 11, 1995

[54] ELECTRONIC TRANSDERMAL DRUG DELIVERY SYSTEM

[75] Inventors: Joseph P. D'Angelo; Henry Schur, both of Miami, Fla.

[73] Assignee: International Medical Associates, Inc., Miami, Fla.

[21] Appl. No.: 3,095

[22] Filed: Jan. 11, 1993

Related U.S. Application Data

[63] Continuation-in-part of Ser. No. 952,049, Sep. 28, 1992, Pat. No. 5,336,213, which is a continuation-in-part of Ser. No. 927,837, Aug. 10, 1992, which is a continuation-in-part of Ser. No. 865,309, Apr. 8, 1992, abandoned.

[51] Int. Cl.$^6$ ............................................. A61F 13/00
[52] U.S. Cl. ................................. 424/449; 424/447; 602/41; 604/20; 606/32
[58] Field of Search ................... 424/449; 602/41; 604/20; 128/419 R; 606/32

[56] References Cited

U.S. PATENT DOCUMENTS

| | | | |
|---|---|---|---|
| 3,161,502 | 9/1961 | Herbig et al. | 420/537 |
| 3,270,100 | 8/1962 | Jolkouski et al. | 264/4 |
| 3,336,155 | 8/1967 | Rowe | 427/212 |
| 3,341,466 | 9/1967 | Brynko et al. | 427/213.35 |
| 3,396,117 | 8/1968 | Schuetze | 428/402.2 |
| 3,405,070 | 10/1968 | Reyes | 264/4.1 |
| 3,567,650 | 3/1971 | Bakan | 427/213.32 |
| 3,797,494 | 3/1974 | Zaffajoni | 424/434 |
| 3,875,074 | 4/1975 | Vassiliades et al. | 428/402.22 |
| 4,145,187 | 3/1979 | Brain et al. | 422/232 |
| 4,207,315 | 6/1980 | Voorhees et al. | 514/47 |
| 4,277,364 | 7/1981 | Shasha et al. | 504/250 |
| 4,391,909 | 7/1983 | Lim | 435/178 |
| 4,422,970 | 12/1983 | Rajadhyausha et al. | 540/533 |
| 4,592,753 | 6/1986 | Panoz | 424/449 |
| 4,666,441 | 5/1987 | Andriola et al. | 424/448 |
| 4,708,716 | 11/1987 | Sibalis | 604/20 |
| 4,743,249 | 5/1988 | Loveland | 424/447 |
| 4,806,355 | 2/1989 | Goosen et al. | 424/424 |
| 4,834,978 | 5/1989 | Nuwayser | 424/448 |
| 4,913,905 | 4/1990 | Fankhauser et al. | 424/449 |
| 4,917,676 | 4/1990 | Heiber et al. | 424/449 |
| 5,028,435 | 7/1991 | Katz et al. | 424/484 |
| 5,032,403 | 7/1991 | Sinnreich | 424/448 |
| 5,042,975 | 8/1991 | Chien et al. | 604/20 |
| 5,064,422 | 11/1991 | Wick | 604/307 |
| 5,064,654 | 11/1991 | Berner et al. | 424/448 |
| 5,071,704 | 12/1991 | Fischel-Ghodsian | 428/354 |

FOREIGN PATENT DOCUMENTS 0252732  1/1988  European Pat. Off.

OTHER PUBLICATIONS

"Retardation by Aminoguanidine of Development of Albuminuria, Mesangial Expansion, and Tissue Fluorescence in Stieptozocia-Induced Diabetic Rat" Soulis-Liparota et al., Diabetes, vol. 40, Oct. 1991, pp. 1328-1334.

(List continued on next page.)

*Primary Examiner*—D. Gabrielle Phelan
*Attorney, Agent, or Firm*—Herbert L. Lerner; Laurence A. Greenberg

[57] ABSTRACT

A drug delivery system for transdermally delivering drugs through a given skin area is provided. The delivery system comprises a collapsible container for containing the drug. The container has a drug release opening. A displaceable member is in engagement with the container for expelling the drug from the container via the release opening. A driver is connected with said displaceable member so as to drive the same towards the collapsible container. Conduits are disposed between the release opening and the skin area for conducting the drug to the skin area. An ultrasonic transducer is disposed in the general conduit area for generating ultrasonic waves aimed at the skin area. An ultrasonic waveform generator drives the transducer and an electric control circuit is connected to the flow control for electrically activating the flow control.

17 Claims, 23 Drawing Sheets

OTHER PUBLICATIONS

Mechanistic Studies of Advanced Glycosylation End Product Inhibition by Aminoguanidine. Edelstein et al, Diabetes, vol. 41, Jan. 1992, pp. 26–29.

Effect of Aminoguanidine on Functional and Structural Abnormalities in Peripheral Nerve of STZ–Induced Diabetic Rats Yagihashi et al, Diabetes, vol. 41, Jan. 1992, pp. 47–52.

Aminoguanidine, a Novel inhibitor of Nitric Oxide Formation, Corbett et al, Diabetes, vol. 41, Apr. 1992, pp. 552–556.

Azone, Chapter 5, vol. II, pp. 63–83 "Transdermal Delivery of Drugs". Effects of Oral and Transdermal Insulin Applications on Blood Glucose Concentration of Mice Liedtke et al, Arzneim.–Forsh./Drug research 40(II) Oct. 8, 1990 pp. 880–883.

Transdermal Insulin Application in Type II Diabetic Patients 1 Results of a Clinical Pilot Study Liedtke et al, Drug Research, 40(II) N1 8, 1990, pp. 884–886.

Direct Current Iontophoretic Transdermal Delivery of Peptide and Protein Drugs Chien et al, Journal of Pharmaceutical Sciences, vol.78, No. 5, May 1989 pp. 376–383.

Potential Novel Methods for Insulin administration, Stephen et al, Biomed. Biochim. 5, 1984, pp. 553–558.

Controlled Release of Drugs: Polymers and Aggregate Systems Morton Rosoff, Chapter 9, pp. 277–303.

Controlled–Release Technology, Lee et al, 1987, pp. 282–350.

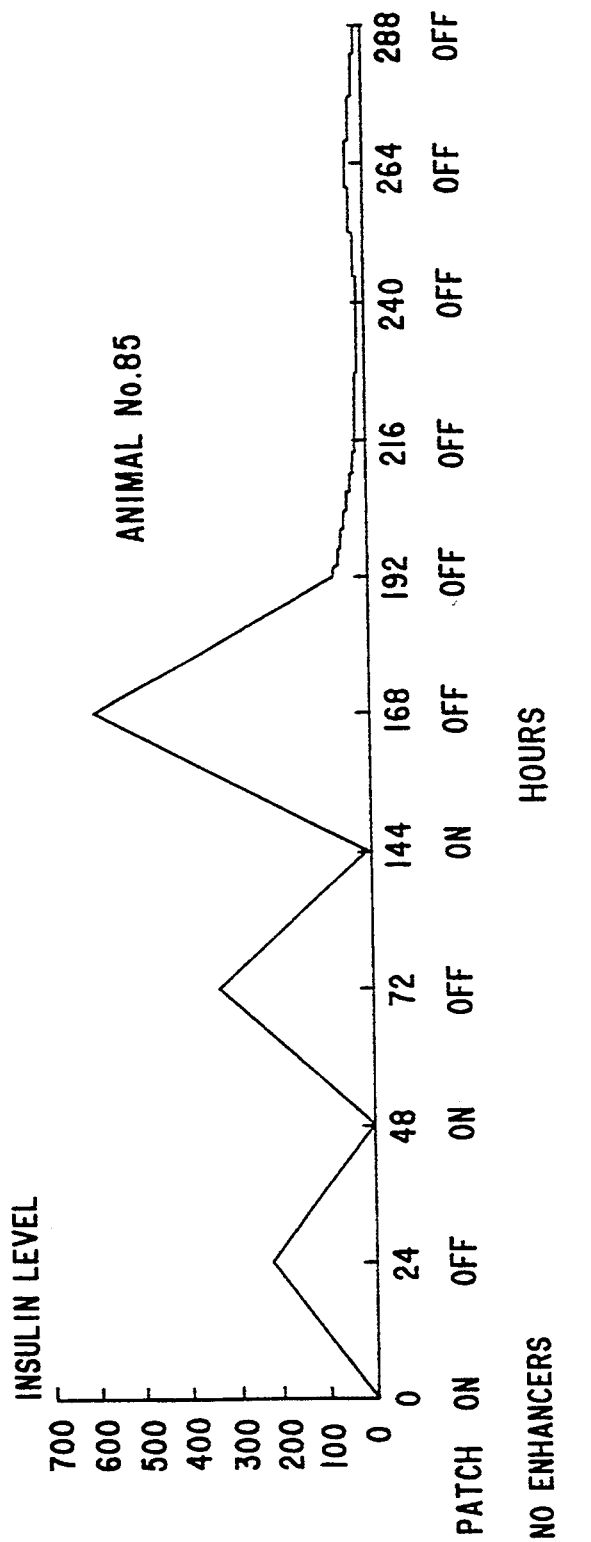

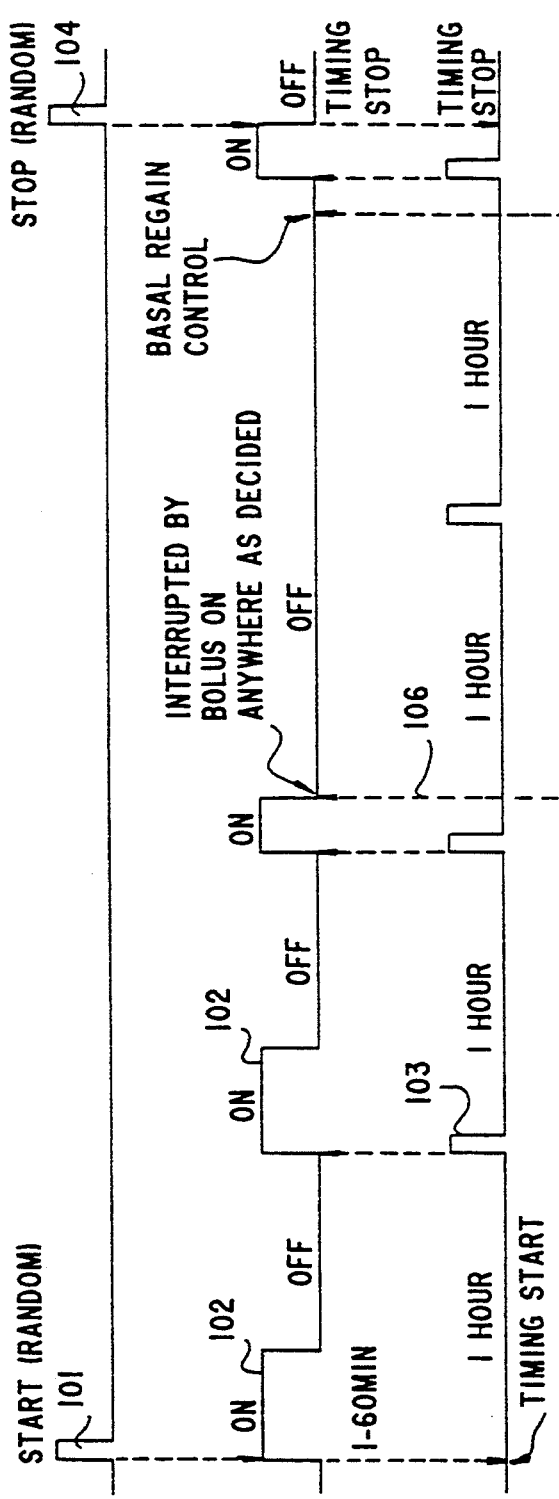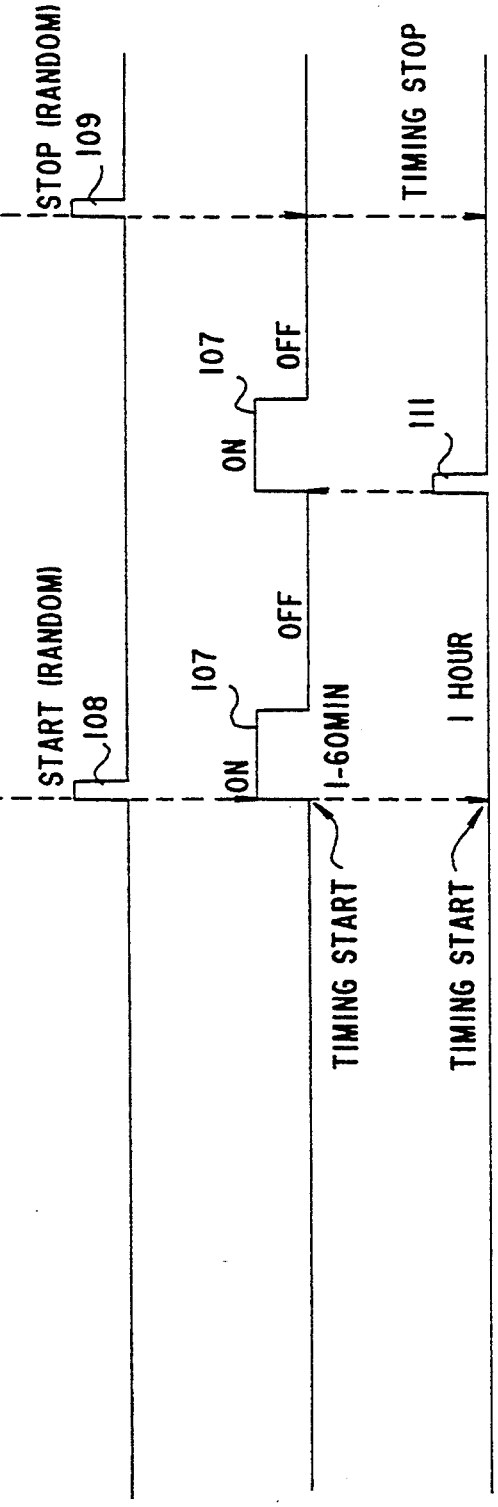

WHEN OUTPUT IS ON
OUTPUT WILL CONTAIN SIGNAL

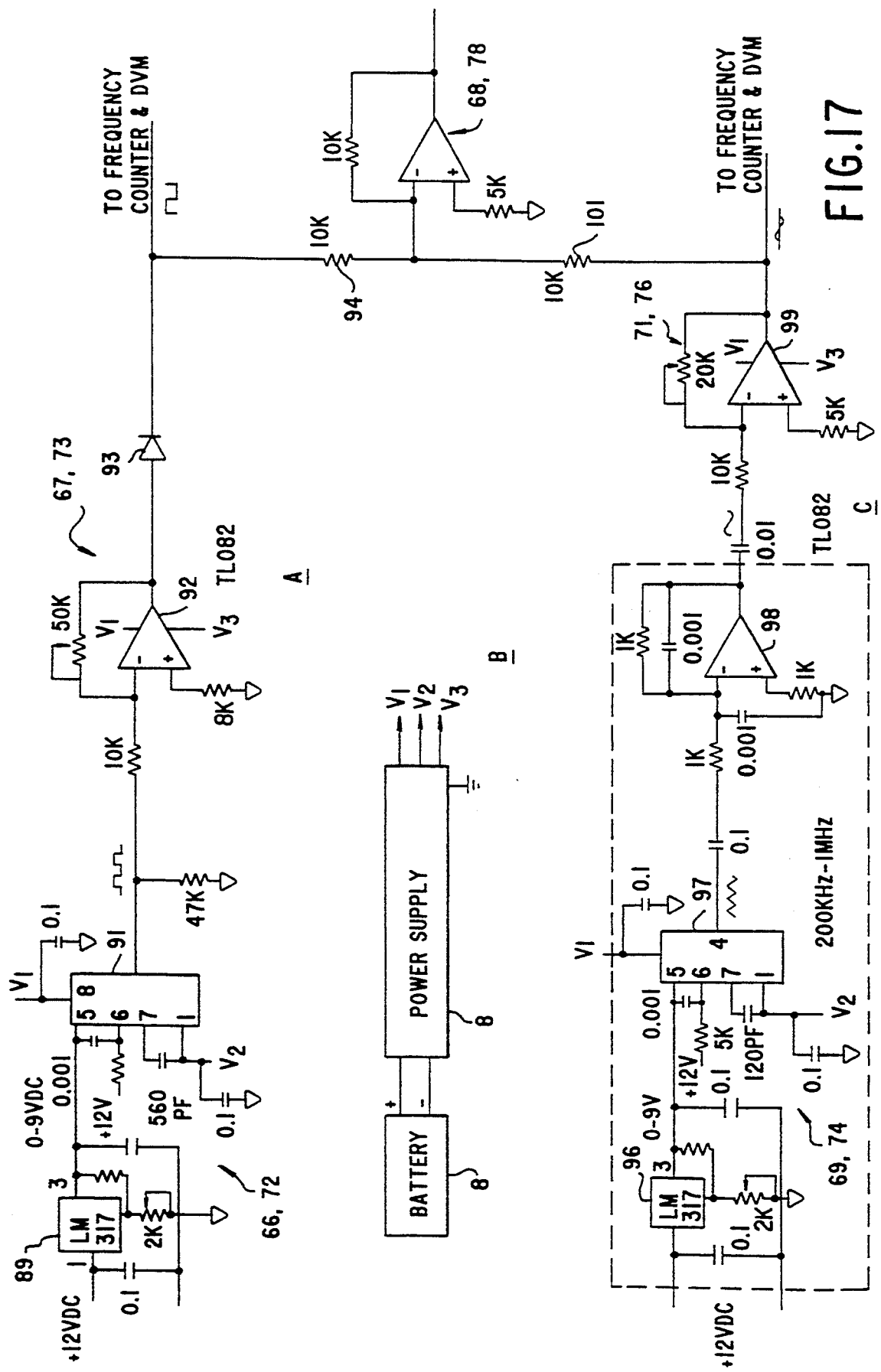

ELECTRONIC TRANSDERMAL DRUG DELIVERY SYSTEM

CROSS-REFERENCE TO RELATED APPLICATIONS

This is a continuation-in-part of application Ser. No. 07/952,049, filed Sep. 28, 1992, now U.S. Pat. No. 5,336,213, which is a continuation-in-part of copending application Ser. No. 07/927,837, filed Aug. 10, 1992, which is a continuation-in-part of application Ser. No. 07/865,309, filed Apr. 8, 1992, now abandoned.

BACKGROUND OF THE INVENTION

1. Field of the Invention

The invention relates to transdermal drug delivery, and more particularly to a delivery systems which allows for the variable dosage and/or multiple dosage of medicament in a patient-controllable or pre-set format.

2. Description of the Related Art

Transdermal drug administration has recently come to the forefront as a useful route for continuous dosing of useful drugs. Nicotin patches, for instance, have recently received very broad popular coverage. Medical/pharmacological science is currently testing a wide variety of applications. Many shortcomings and disadvantages of oral or intravenous infusion of medicament are obviated by transdermal application of the drugs.

In general terms, a patch is adhered to a clear area of the skin and the drug is continually absorbed through the skin into the bloodstream for systemic distribution. The skin is particularly useful as it presents large areas for drug administration, as the skin is the largest organ of the body. The utility of such a mode of administration has been demonstrated to those skilled in the art, as described, for example, in my above-noted copending applications.

As the human skin is a very powerful barrier organism, a number of problems must be overcome to enable transdermal drug delivery. Transdermal drug delivery has been demonstrated to be effected by pharmaceutical skin permeation enhancers and electromagnetic stimulation. As described by William R. Good in "Controlled-Release Technology", ACS Symposium Series 348, American Chemical Society, Washington, D.C. 1987, chapters 21-24, the three essentially different approaches may be categorized as physical, chemical and biochemical. The physical category includes iontophoresis, ultrasonic energy and thermal energy, for example.

Iontophoresis, the transfer of drugs through the skin by the introduction of a dc current, was first postulated by S. LeDuc in 1908. At this time however, it has lost favor because of various problems associated with its use. None of the commercially available devices, as far a understood, utilize iontophoresis. The most important problem associated with the technique is its tendency to cause burns under the electrodes. While this is usually due to operator error, burns can occur even with proper technique. Another inconvenience is the messiness of the procedure. Finally, the major drawback to dc iontophoresis is the uncertainty and lack of consistent results.

U.S. Pat. No. 4,592,753 to Panoz describes a transdermal drug delivery device which allows the transdermal application of nitroglycerin. The transdermal or percutaneous delivery is effected by thermal energy released by the nitroglycerin under increased pressure in the drug pouch and during its diffusion into a zone of lower concentration. The wrist band of Panoz provides the pressure on the drug pouch, so that the transdermal delivery is not timed by the device. Also, no accurate control of drug amounts is possible.

SUMMARY OF THE INVENTION

It is accordingly an object of the invention to provide an electronic transdermal drug delivery system which overcomes the hereinafore-mentioned disadvantages of the heretoforeknown devices of this general type and which achieves a level or convenience and control which has not before been known.

With the foregoing and other objects in view there is provided, in accordance with the invention, a drug delivery system for transdermally delivering drugs through a given skin area, comprising a collapsible container for containing the drug, the container having a drug release opening; a displaceable member in engagement with the container for expelling the drug from the container via the release opening; drive means connected with the displaceable member; conduit means disposed between the release opening and the skin area for conducting the drug to the skin area; an ultrasonic transducer in the conduit means for generating ultrasonic waves aimed at the skin area; an ultrasonic waveform generator drivingly connected to the transducer and an electric control circuit connected to the drive means means for electrically activating the drive means.

The goal of developing a pulse delivery system is to achieve a level of convenience and control, without the above mentioned drawbacks. A pulse delivery system is an electronic system which applies a pulse to the patient without any direct electrical contact. There are two major types of pulses available which are used in the context of this invention:

1) A sound pulse, which is basically a pressure wave, and
2) A sonic pulse train directed at a skin area selected for transdermal infusion, particularly a pressure waves. The pulse train is especially effective when composed of a sine wave superimposede on a square wave signal driving a sonic transducer.

Both types of waves can be generated with the same electronic circuits. The type of wave produced depends upon the selection of the specific transducer. Any transducer which uses a coil of wire to produce a sound will create such waves. A piezo-electric device will produce pressure.

At the current level of information available to the inventors, it appears that a piezzo-electric device will meet all of the needs. Further testing is being done. However, such testing should not be construed as being undue experimentation, since tests of this nature are easily performed by the person of skill in the art.

Although a detailed theory of cell behavior does not appear to be crucial in this context, the following is believed to be correct: Basically, cells may be said to act like sacks of liquid. In their resting state, cells are subject to dipole and quadrupole moments, i.e. they have a positive charge outside and a negative charge inside. This is caused by an excess of sodium ions (Na+) outside and a smaller number of potassium ions (K+) inside. When excited by an external stimulus (electric field or pressure), the cell responds by allowing large numbers of Na+ Ions to enter the cell, resulting in a change of polarity of the cell. This is generally referred to as an action potential. The cell then reverts to its resting state. As best understood, that exchange of Na+ and K+ ions may in part be responsible for the ability of current or pulse energy to introduce drugs to the body through the skin.

The following must be taken into consideration when choosing a given drug: In order for a compound to physiologically penetrate a membrane it must be biphasic, i.e. it is soluble in both water and oil. A water factor is necessary for good ion formation in solution, and a fat factor is necessary for good tissue penetration and permeability. Virtually all hydrochloride selections of therapeutic drugs meet this requirement. Drugs which do not meet this need may be made more useful by the addition of a surfactant to serve as a bridge.

The drug vehicle must also be considered. It should have very few ions that compete with the drug itself, also it should totally wet the treatment area without forming bubbles. Finally it should be chemically stable and inert, as well as hypoallergenic.

In accordance with another feature of the invention, there is provided a housing, and a cartridge in the housing releasably attached to the housing, wherein the cartridge includes the collapsible container, the displaceable member, the drive means, and the conduit means.

In accordance with a further feature of the invention, there is provided a first set of electrical contacts for releasably inter-connecting the flow control means with the electrical control circuit and a second set of electrical contacts for releasably connecting the ultrasonic waveform generator with the ultrasonic transducer.

In accordance with an added feature of the invention, there are provided in the drive means a coil spring disposed in the cartridge in operative engagement with the displaceable member for applying pressure in the container.

In accordance with an additional feature of the invention, there are provided in the drive means a double spring disposed in the cartridge in operative engagement with the displaceable member for applying pressure on the container.

In accordance with still another feature of the invention, there are provided in the cartridge an electric battery; and a third set of electrical contacts for releasably connecting the battery with the electrical control circuit and with the ultrasonic waveform generator.

In accordance with still a further feature of the invention, the cartridge has a cylindrical shape, and the housing has a cylindrical hole for receiving the cartridge.

In accordance with still an added feature of the invention, there are provided in the housing an electrical watch display, and an electrical timing circuit in the electrical control circuit connected to the watch display.

In accordance with still an additional feature of the invention, there are provided flow control means in the conduit means for controlling the flow of drugs to the skin area, the flow control means including a flow control valve, a shape memory alloy member in operative engagement with the control valve, and a fourth set of electrical contacts for releasably connecting the shape memory alloy member with the electrical control circuit for electrically controlling the control valve.

In accordance with yet another feature of the invention, the housing is shaped like an electric wrist watch, and including a watch band connected to the housing for attaching the housing to a wrist.

In accordance with yet a further feature of the invention, there is provided a pivotable tab attached to the cartridge, the pivotable tab having an extended position facing away from the cartridge for grasping the cartridge, and a closed position, closed into the cartridge.

In accordance with yet an added feature of the invention, there are provided in the conduit means a skin area interface membrane for contacting the skin area, a layer of transfer gel in contact with the interface membrane, an open cell foam body having one side connected with the transfer gel, a medicament distribution chamber communicating at one side with the foam body and at an opposite side with the flow control means.

In accordance with yet an additional feature of the invention, the transducer is a planar piezo-electric disc electrically connected with the ultrasonic waveform generator.

In accordance with again another feature of the invention, there are provided in the ultrasonic waveform generator at least one sine wave generator, at least one square wave generator, a summing circuit having respective inputs connected to the sine wave generator and to the square wave generator for generating a superimposed signal of the sine wave and the square wave connected to the transducer.

In accordance with again a further feature of the invention, the timing circuit is operative for activating the waveform generator in alternating on and off states in programmed sequence.

In accordance with again an added feature of the invention, there are provided in the timing circuit EEPROM means for storing at least one timing program for timing the programmed sequence.

In accordance with again an additional feature of the invention, there are provided stored in the EEPROM means at least one basal timing sequence and at least one bolus timing sequence.

In accordance with another feature of the invention, there is provided on the housing a plurality of control knobs connected to the electrical control circuit, wherein one of the control knobs is operative for activating the basal timing sequence, and a second one of the control knobs is operative for activating the bolus timing sequence.

In accordance with a further feature of the invention, the bolus sequence overrides the basal timing sequence.

In accordance with an added feature of the invention, the bolus timing sequence is time-limited.

In accordance with an additional feature of the invention, there are provided an access port connected to the EEPROM means, the access port operative for accessing external programming means for entering timing programs into the EEPROM.

In accordance with still another feature of the invention, there is provided in the electrical control circuit an alarm system for generating an alarm in case of failure of the electrical control circuit.

In accordance with still a further feature of the invention, there is provided an audible alarm transmitter connected to the alarm system for generating an audible alarm in case of failure of the electrical control system.

With the objects of the invention in view there is also provided, in accordance with the invention, an assembly for the transdermal administration of a drug to a patient, which comprises a base unit having a timer and electrical connections for issuing electronic timing information from the timer; and a drug administration unit electrically connected to the base unit, the drug administration unit having a housing defining a space therein for receiving a drug and the housing having drug dispensing conduit means formed therein, a skin-contacting surface to be placed on a patient's skin, and dispensing means for selectively causing time-dependent dispensing of a drug from the space in the housing through the conduit means to the skin-contacting surface and to the patient's skin.

In accordance with a further feature of the invention, the dispensing means include valve means disposed in the conduit means for selectively closing and opening the conduit means.

In accordance with an added feature of the invention, there are provided means for generating pressure waves in an upper sonic and supersonic range at the skin contacting surface for facilitating transdermal absorption of the drug dispensed to the skin contacting surface.

In accordance with an additional feature of the invention, the pressure wave generating means include a transducer disposed closely adjacent the skin contacting surface, and circuit means connected to the transducer operative for driving the transducer at a given frequency.

In accordance with a concomitant feature of the invention, the circuit means include wave form generator means for generating an electronic signal formed of a square wave in a frequency range of between 20 KHz and 100 KHz and of a sine wave superimposed thereon in a frequency range of between 200 KHz and 1 MHz.

Other features which are considered as characteristic for the invention are set forth in the appended claims.

Although the invention is illustrated and described herein as embodied in an electronic transdermal drug delivery system, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

FIG. 10 is a diagram of exemplary animal test results;

FIG. 15(a-g) shows timing patterns for on/off pulse distribution;

FIG. 17 is a diagram of a detail of a basic timing and waveform generating circuit according to the invention.

DESCRIPTION OF THE PREFERRED EMBODIMENTS

Figure 1:
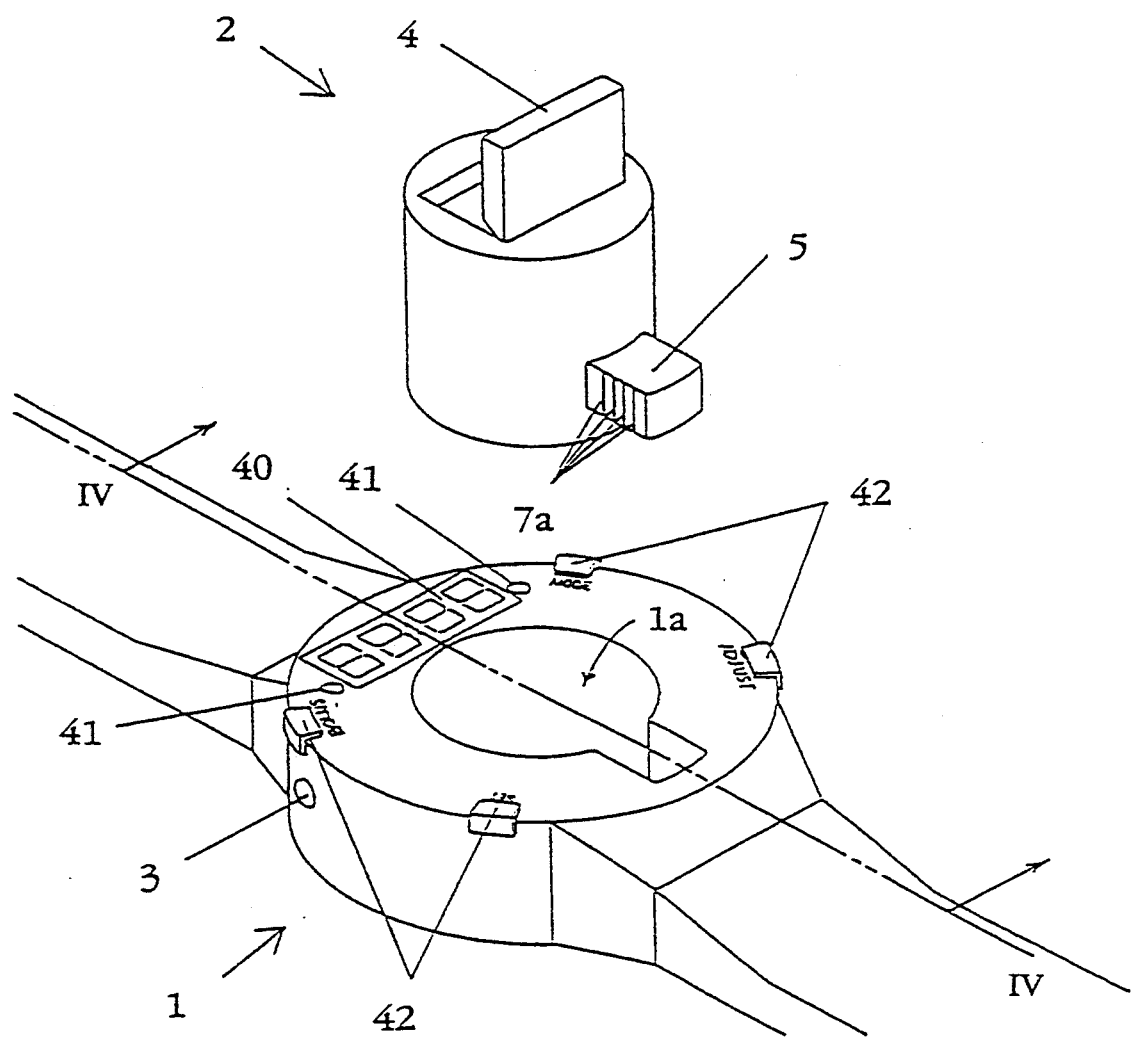
FIG. 1 is a perspective view of the device according to the invention.

Referring now to the figures of the drawing in detail and first, particularly, to FIG. 1 thereof, there is seen a wristband with an electronic base unit 1. As will be explained in the following, the electronic base unit 1 includes all of the necessary components of a wristwatch. A medicament cartridge 2 is placed in a center opening 1a provided in the base unit 1. The cartridge 2 is provided with a cartridge grasp tab 4. The cartridge 2 is held on the tab 4, inserted in the center opening 1a, and then rotated clockwise, as seen from the top.

Figure 2:
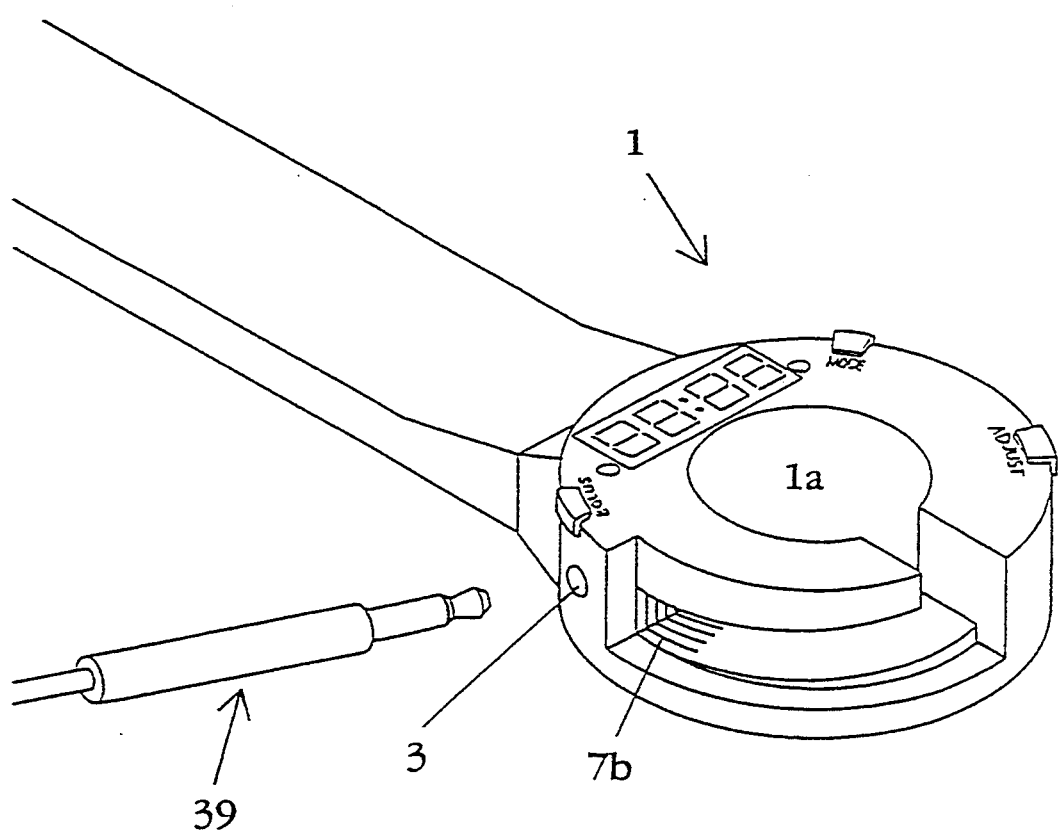
FIG. 2 is a partly broken-away, perspective view thereof.

As seen in FIG. 2, when the cartridge 2 is inserted in the center opening 1a and rotated until it comes to a stop, an electrical contact set 7a provided on a cartridge stem 5 come into contact with an electrical contact set 7b in the base unit 1.

The base unit is provided with a interface port 3. The port 3 allows direct direct programming access to the electronics of the base unit, by way of a computer interface jack 39. Electronic programming, such as the programming of an EEPROM through the interface jack 39 and the port 3 is well within the level of ordinary engineering skill in the electronics art. No detailed description of that feature is thus believed to be necessary.

Again referring to FIG. 1, the base unit is provided with user-operated control knobs 42. The control knobs 42 are used for accessing certain timer and display functions, which are generally known in the context of electronic watches. The knob 42 labeled BOLUS is of specific importance in this invention. As explained in the description of the electronic circuitry, the BOLUS button is used to override the timed dispensing of drug actives, referred to a BASAL administration which is governed by the programmed timer functions.

Figure 3A:
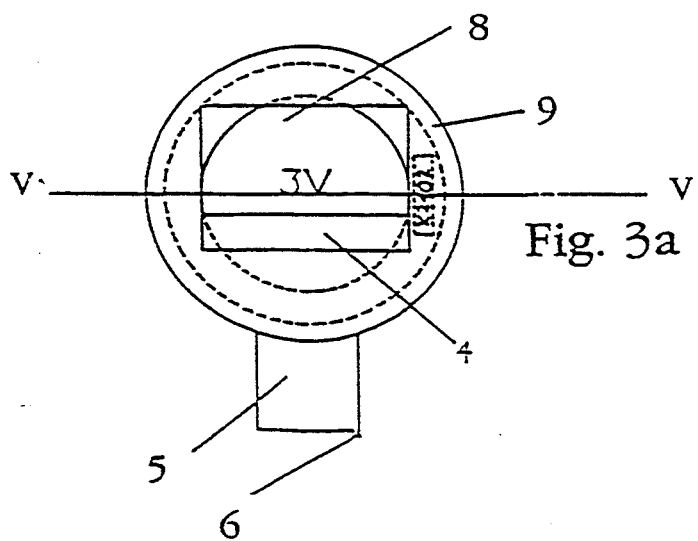
FIG. 3a is a top-plan view of a medicament cartridge.
Figure 3B:
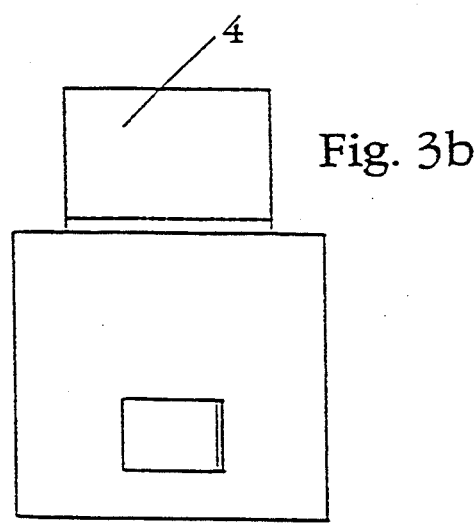
FIG. 3b is a side-elevational view thereof.
Figure 3C:
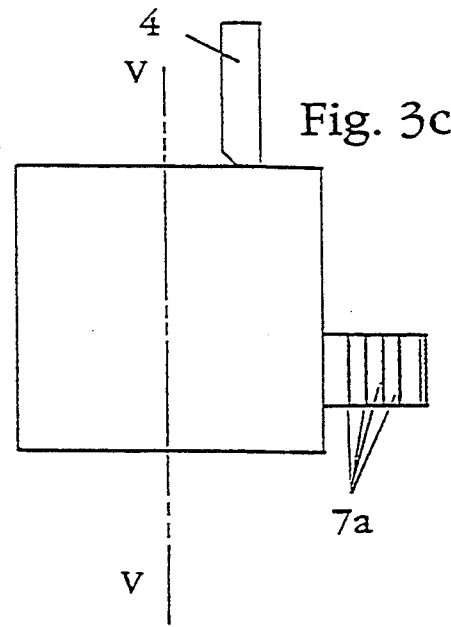
FIG. 3c is a front-elevational view thereof.

Referring now to FIGS. 3a, 3b and 3c, which illustrate the cartridge 2 in top plan, front and right-side elevational views, respectively, a battery 8 is provided. In this embodiment, the battery 8 is a standard 3 volt dc battery. The tab 4 which is used for manually inserting and rotating the cartridge 2 in the base opening 1a, may be pivoted into a horizontal position as shown by a dashed line in FIG. 3c.

Figure 4:
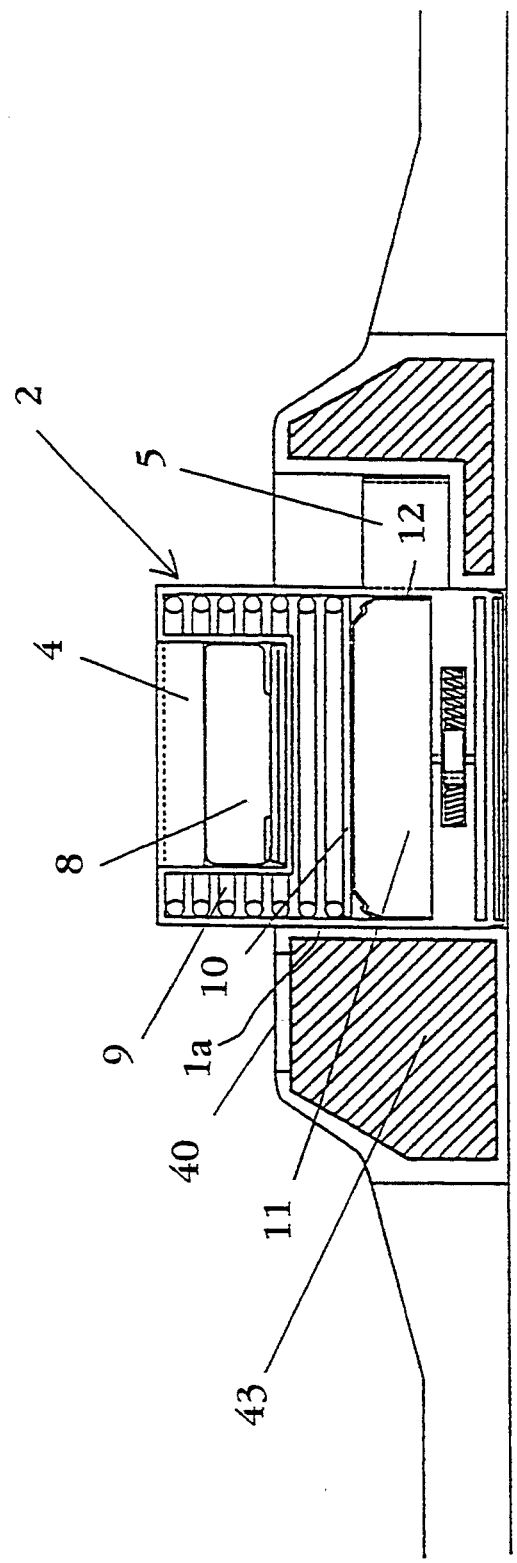
FIG. 4 is a cross-sectional view of the base unit with the medicament cartridge placed therein, the view taken of a vertical section along the line IV—IV of FIG. 1, in the direction of the arrows.
Figure 5A:
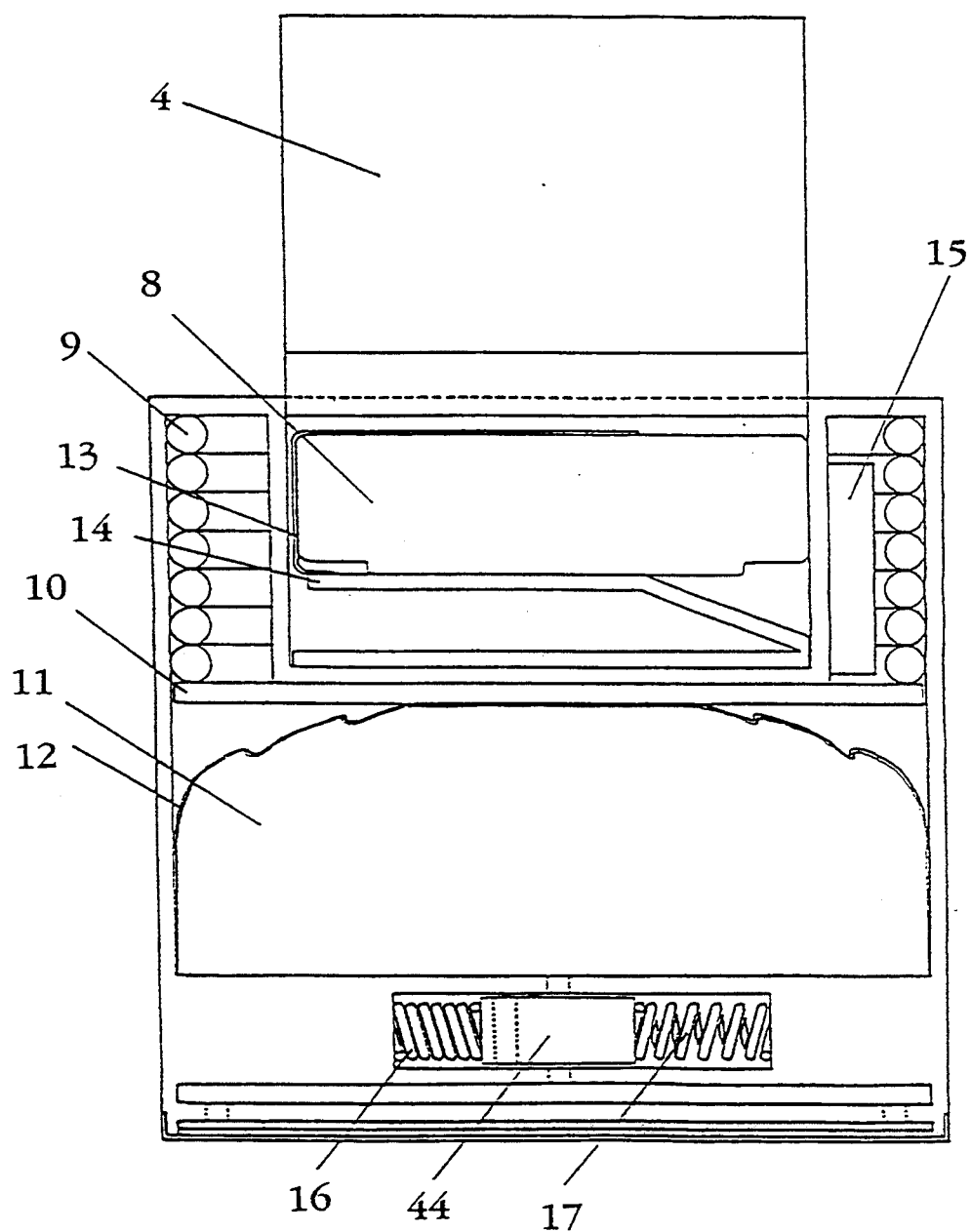
FIG. 5a is a cross-sectional view of the medicament cartridge of FIGS. 3a-3c, taken along the line V—V of FIGS. 3a and 3c.
Figure 5B:
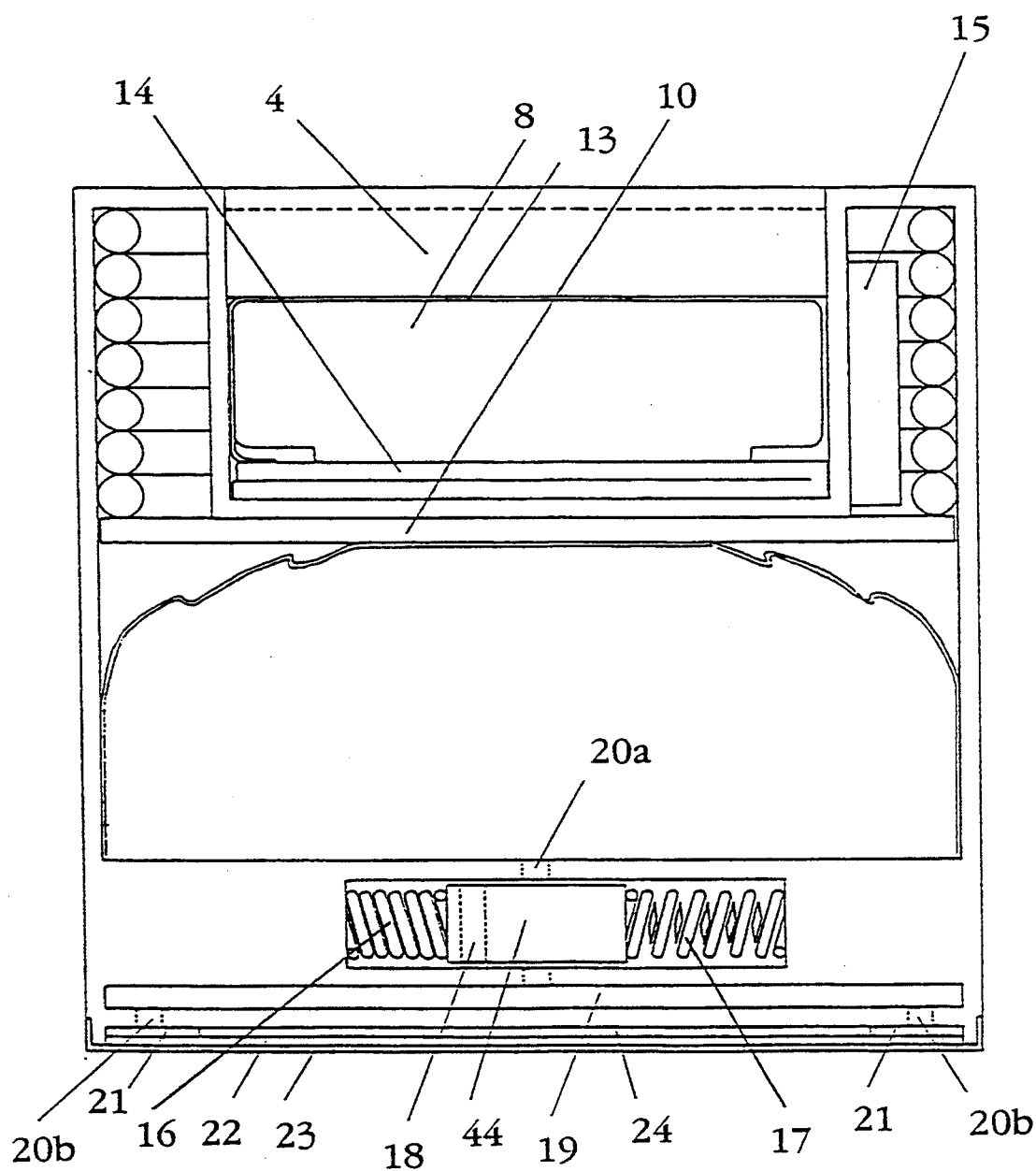
FIG. 5b is a view similar to FIG. 5a, but showing the cartridge with a closed tab.
Figure 5C:
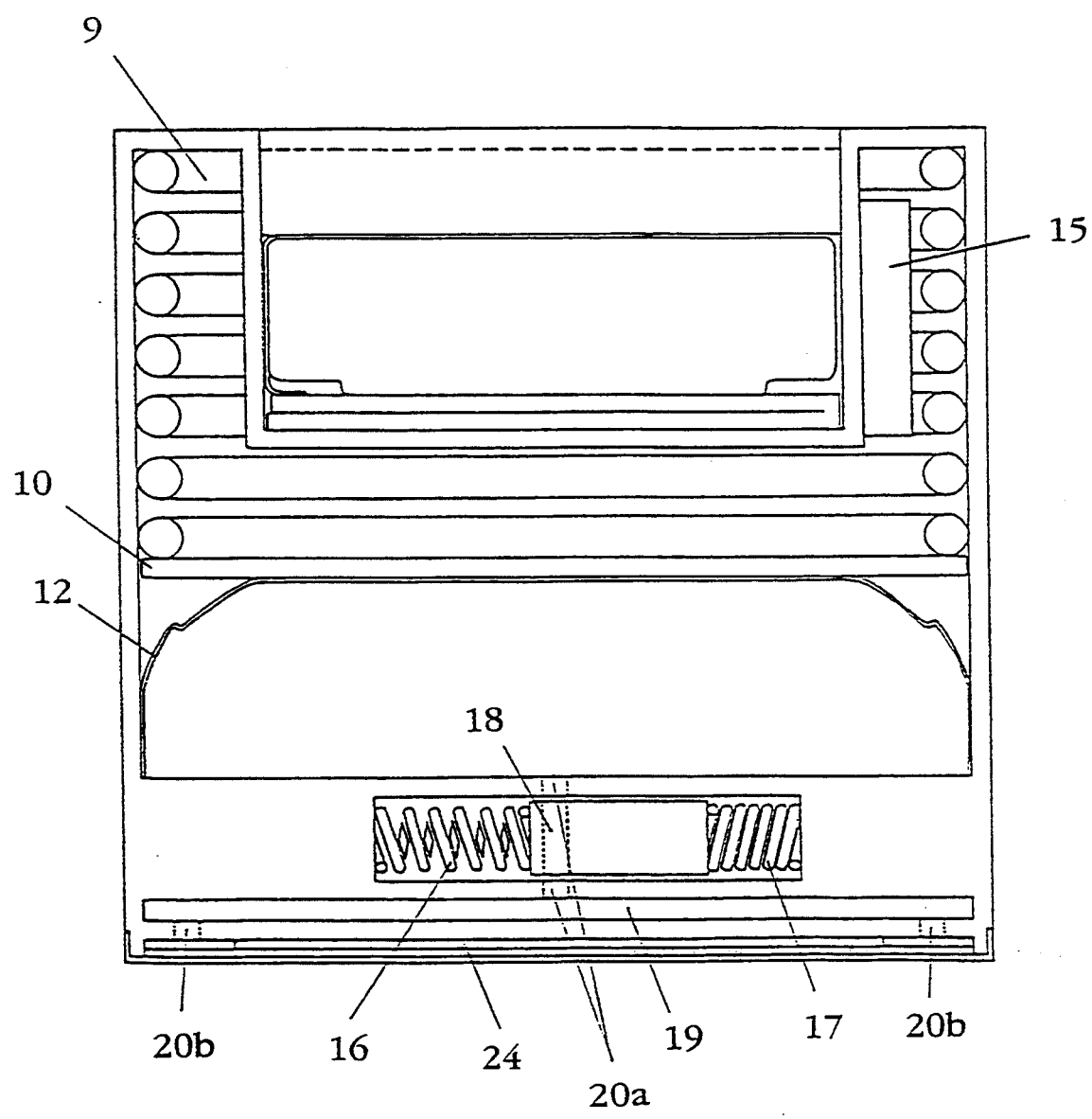
FIG. 5c is a view similar to FIG. 5b, but showing the medicament dispensing valve in an open position.
Figure 5D:
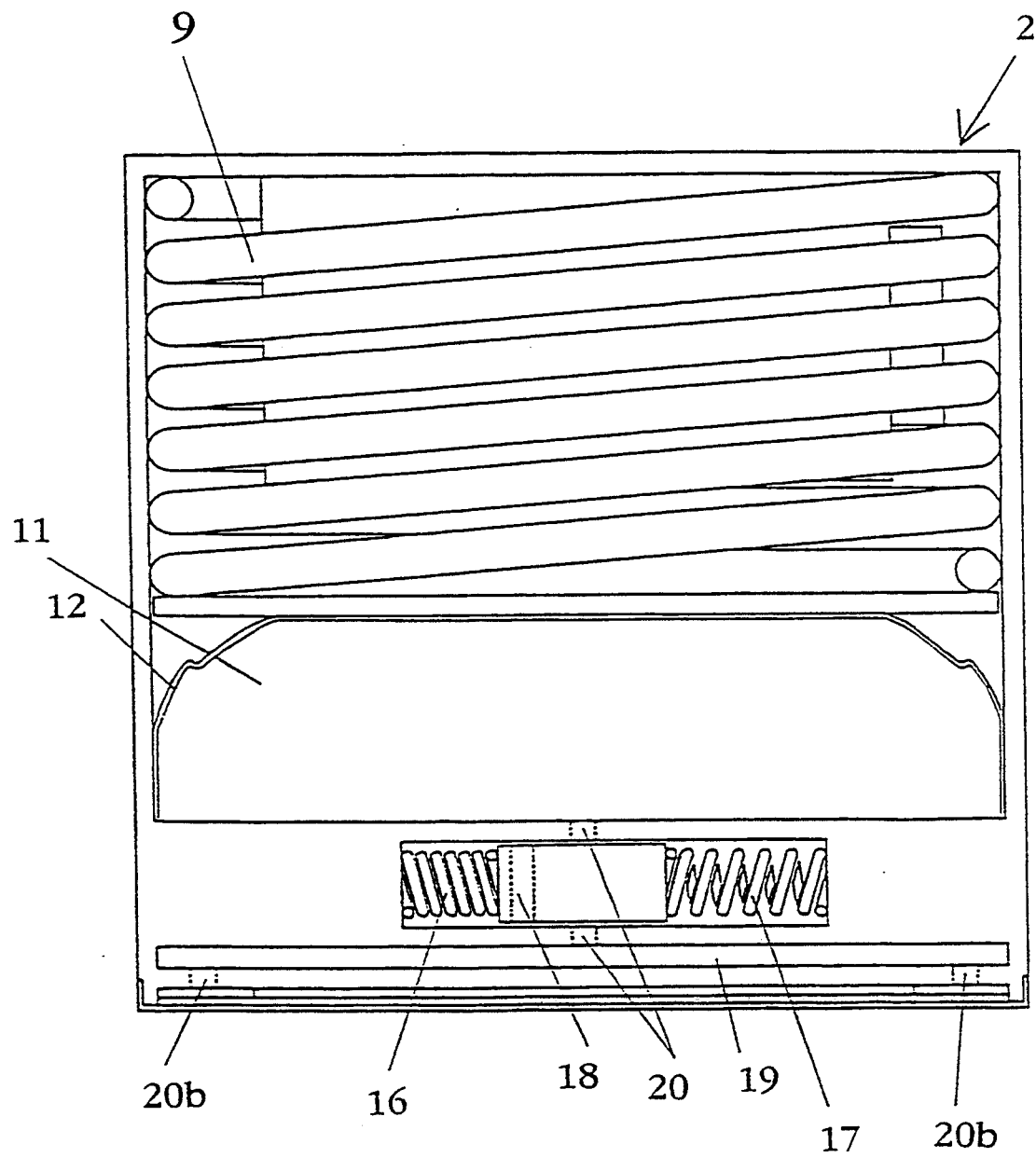
FIG. 5d is a view similar to FIGS. 5a and 5b.

The horizontal position of the tab 4 is shown in FIG. 4, for instance. Also shown in that figure, wherein the cartridge 2 has been inserted in the opening 1a, but not yet rotated clockwise, is a compression spring 9 which biases a spring plate 10 downward towards a medicament 11 which is held in a collapsible medicament pouch or medicament enclosure 12.

The cartridge stem 5 is provided with a small protrusion or cartridge stem flap 6, as best seen in FIG. 3a. The stem flap meshes in non-illustrated serrations on an inside surface of a wall of the base unit 1 which is cut away in FIG. 2. The stem flap 6 secures the cartridge 2 in the base unit 1, in that it prevents the accidental rotation thereof which would cause the electrical contacts 7a and 7b to become disconnected.

With reference to FIGS. 5a–5d, the spring 9 and the spring plate 10 ensure positive pressure on the medicament enclosure 12, so that medication is administered even when the electronic wristband 1 is turned upside down. Contacts for the battery 8 are provided in a conventional manner, i.e. by means of a battery contact 13 and a battery flex plate 14. A ROM chip 15, the function of which will be explained in the following text and in the description of the circuitry, is placed in a space between the battery compartment and the compression spring 9.

The medicament enclosure 12 is closed off with a valve cylinder 44. A valve cylinder conduit 18, when it is aligned with medicament passage conduits 20a, allows the medicament 11 to flow into a capillary distribution chamber 19. A shape memory alloy spring 16 is used to push the valve cylinder 44, i.e. the conduit 18, into alignment with the medicament conduits 20, against the biasing force of a biasing spring 17. The shape memory alloy spring 16 currently used in applicants' embodiments 20a, is a closed-end NiTi spring manufactured by, for example, the Raychem Group.

Shape memory alloys, after an apparent plastic deformation, return to their original shape when heated. This appears to be caused by a phase change, which is known as martensitic transformation. Martensite forms on cooling from the high temperature phase, which is referred to as the austenite phase, by a shear-type process. The alloy is easily deformed in the martensitic phase. When the deformed martensite in a shape memory alloy is heated, it reverts to austenite. The intermetallic compound NiTi (with about 50% nickel) is considered the standard alloy exhibiting the shape memory effect. The specified transition temperature of the alloy is given as approximately 70° C.

When the valve cylinder conduit 18 is aligned with the medicament passage conduits 20a provided in the wall below the medicament enclosure 12, medicament is allowed to flow into a capillary distribution chamber 19. The medicament flows outwardly in the distribution chamber 19, primarily by capillary action, and reaches a plurality of annularly distributed medicament conduits 20b. From the conduits 20b, the medicament reaches an open-cell foam ring 21 or annular sponge 21, which, in turn, transfers the medicament into a transfer gel 22 and then into an interface membrane 23. From the interface membrane 23, which may be referred to as a skin/patch interface, the medicament enters the skin of the patient.

As noted above, the transdermal application of the medicament 11 is effected by superimposed sonic waves, which are created through a transducer 24 connected to a signal generator described below. The transducer 24 is coaxially disposed inside the annular sponge 21, directly above the transfer gel layer 22.

Figure 6A:
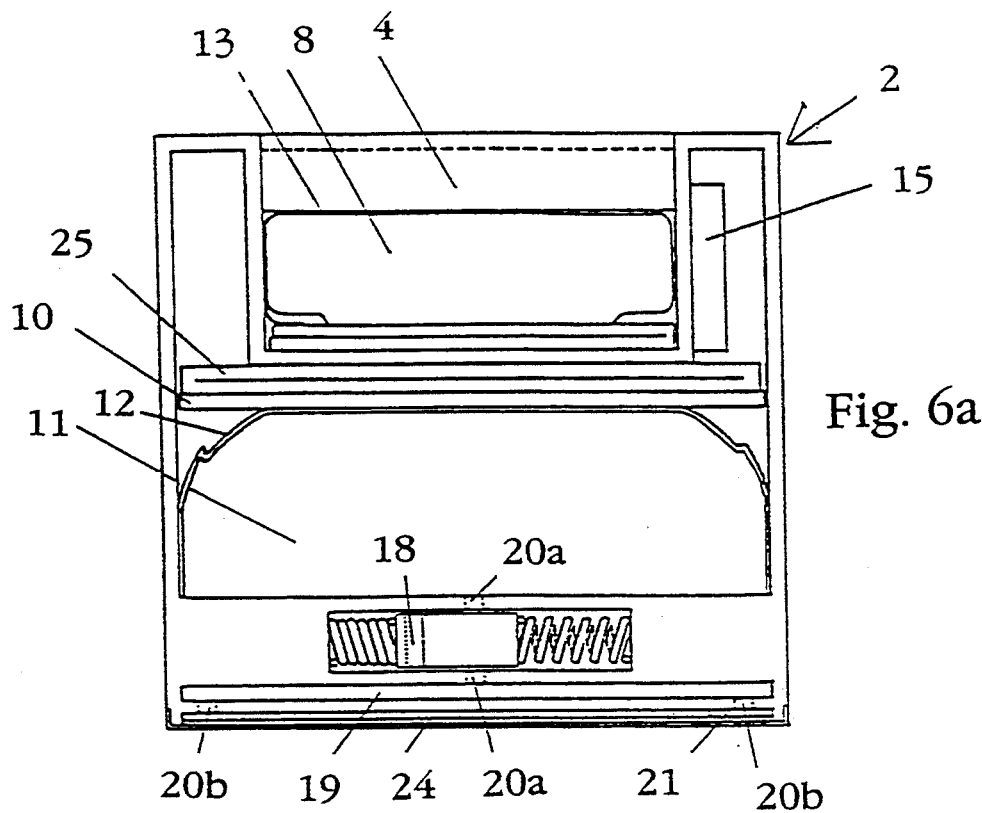
FIG. 6a is a view similar to FIG. 5b of a second embodiment of the medicament cartridge.
Figure 6B:
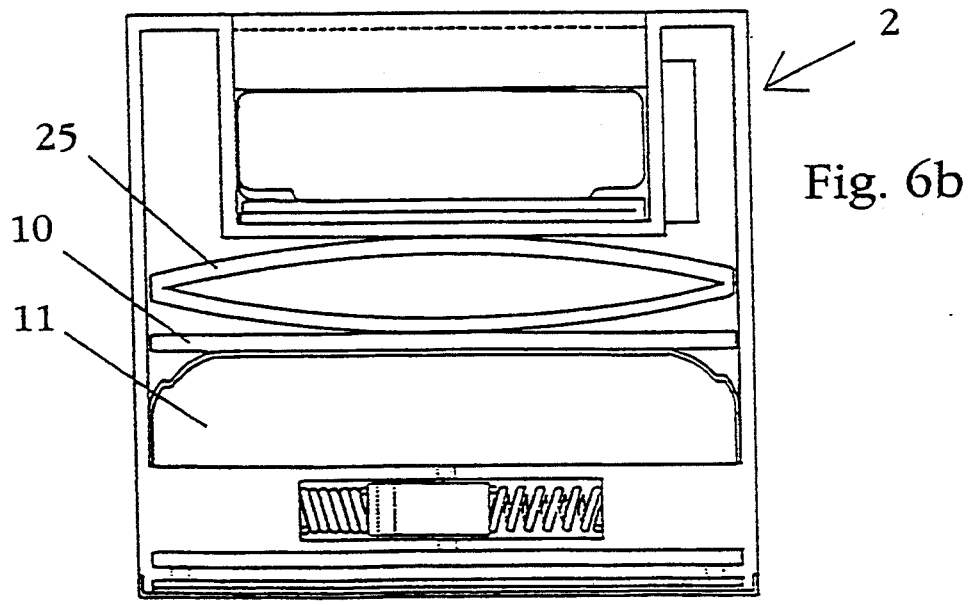
FIG. 6b is a view of the cartridge of FIG. 6a with a partly relaxed pressure spring.

A second embodiment of the medicament cartridge 2 is shown in FIGS. 6a and 6b. A double-leaf spring 25 is put in place of the compression spring 9. The spring constant of the spring 25 is chosen in accordance with the required dispensing pressure, i.e. in dependence on the rigidity of the drug enclosure 12, the viscosity of the drug 11, the size of the dispensing conduit 20a and the valve conduit 18. Due to the capillary action in the capillary chamber 19 and the conduits 20b, a spring pressure will generally suffice when gravitational force can be overcome by the medicament in case the device is turned upside down. Nevertheless, the device is also applicable in a micro-gravity environment, such as in space flight.

Figure 7A:
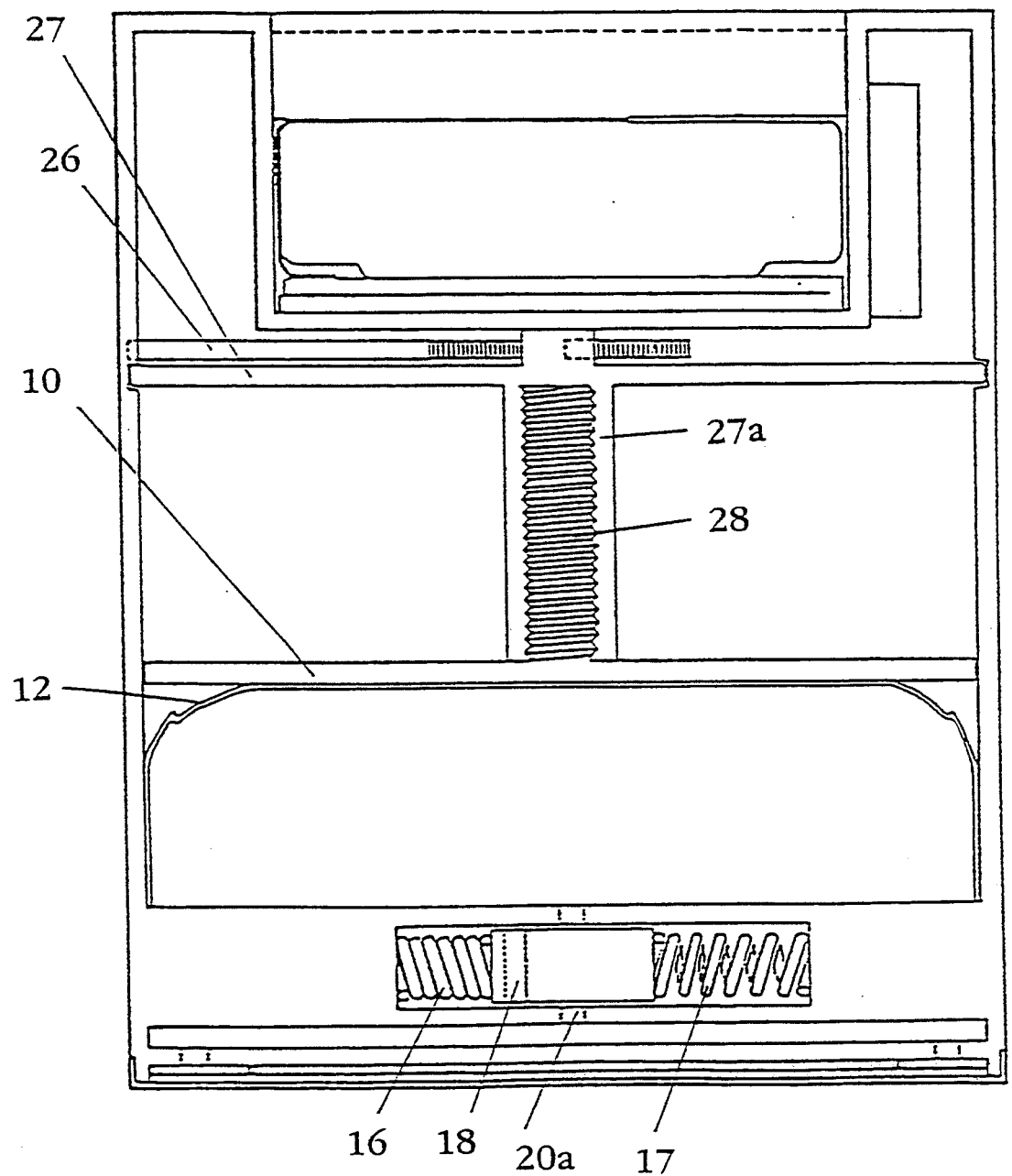
FIG. 7a is a cross-sectional view of a third embodiment of the medicament cartridge, showing a fully coiled dispensing spring and a filled medicament pouch.
Figure 7B:
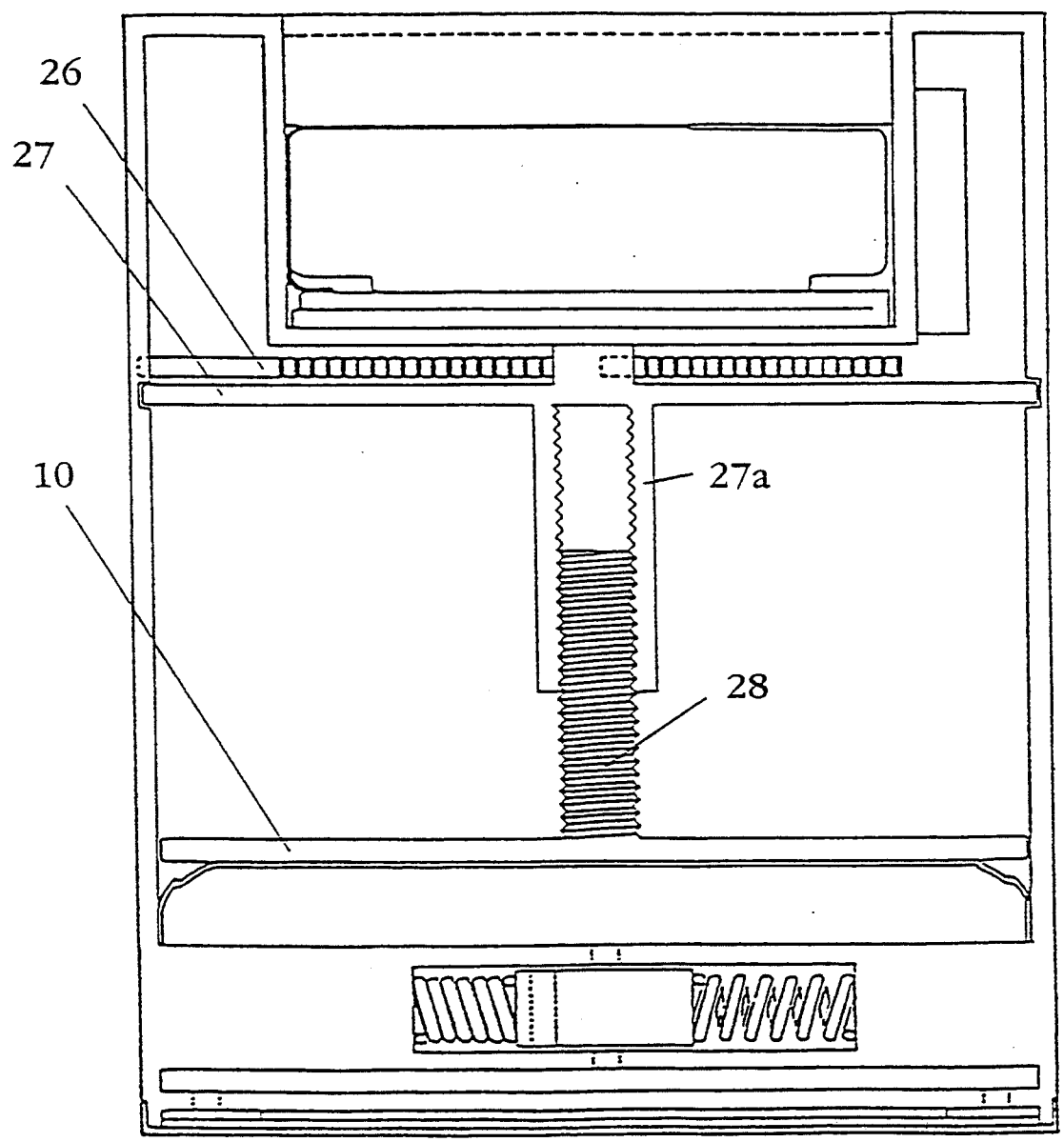
FIG. 7b is a view of the cartridge of FIG. 7a with a partly uncoiled spring and a partly empty medicament pouch.

A third embodiment of the medicament cartridge 2 is shown in FIGS. 7a and 7b. The pressure on the medicament enclosure is created by a constant force spring 26, or coil spring. The coil spring 26 is anchored in the housing of the cartridge and its center is attached to a center knob on a rotating plate 27. The rotating plate 27 rotates within the cartridge housing. An internally threaded stem 27a, which is formed on a lower surface of the rotating plate 27 meshes with a bolt 28 provided on the spring plate 10. The spring plate 10 does not rotate within the housing, so that a rotation of the plate 27 will be translated to a linear (downward) movement of the spring plate 10. The torque applied by the coiled spring 26 on the rotating plate 27 is balanced by the reaction force which the medicament enclosure 12 places on the spring plate 10. Due to the increased pressure on the medicament 11, which is caused by the biasing force of the coiled spring 26, the drug will flow from the dispensing conduit 20a, when the valve conduit 18 is in alignment therewith.

Figure 8:
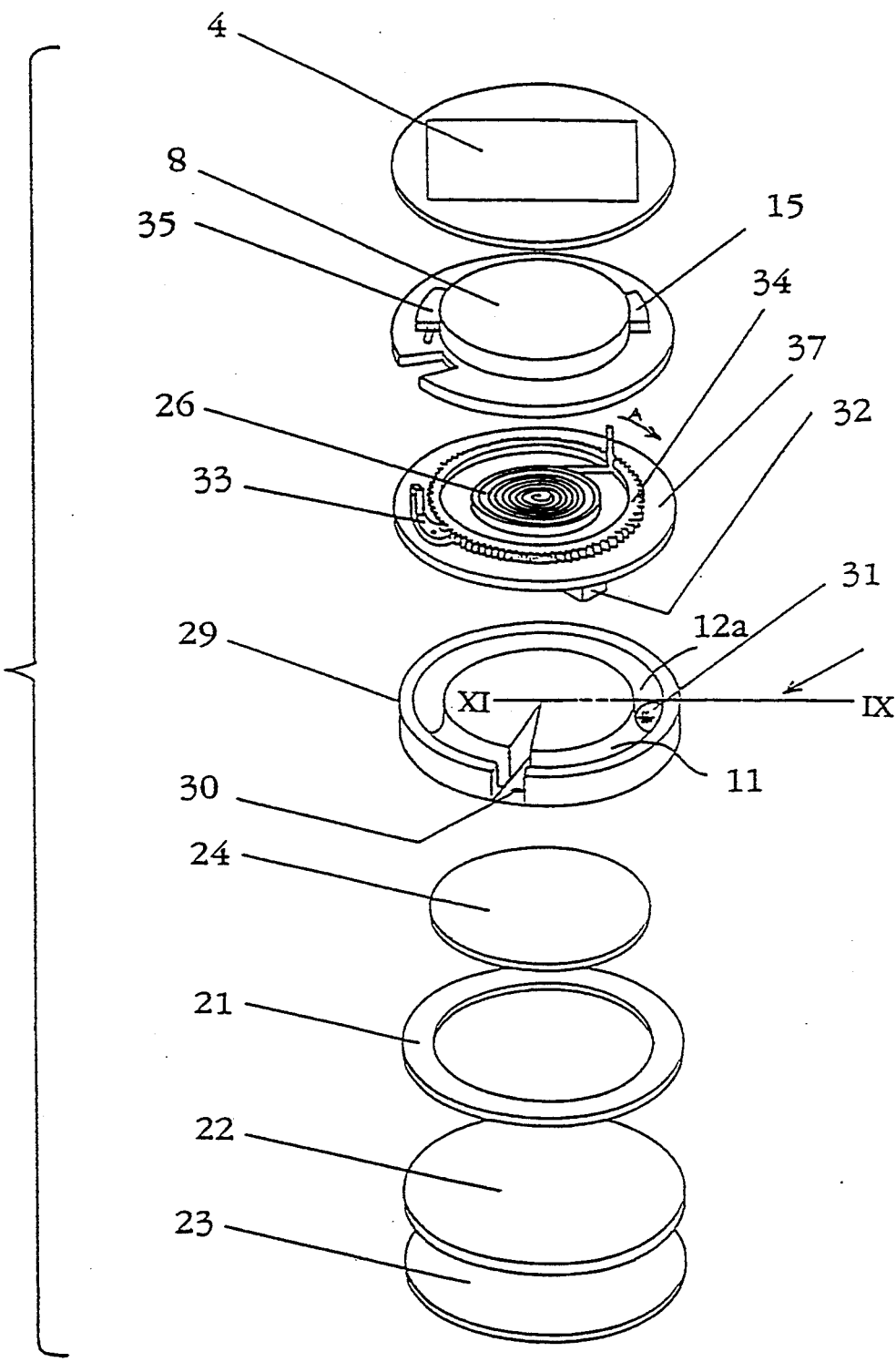
FIG. 8 is a perspective, exploded view of a fourth embodiment of the medicament cartridge which utilizes a perastaltic pump configuration.
Figure 9:
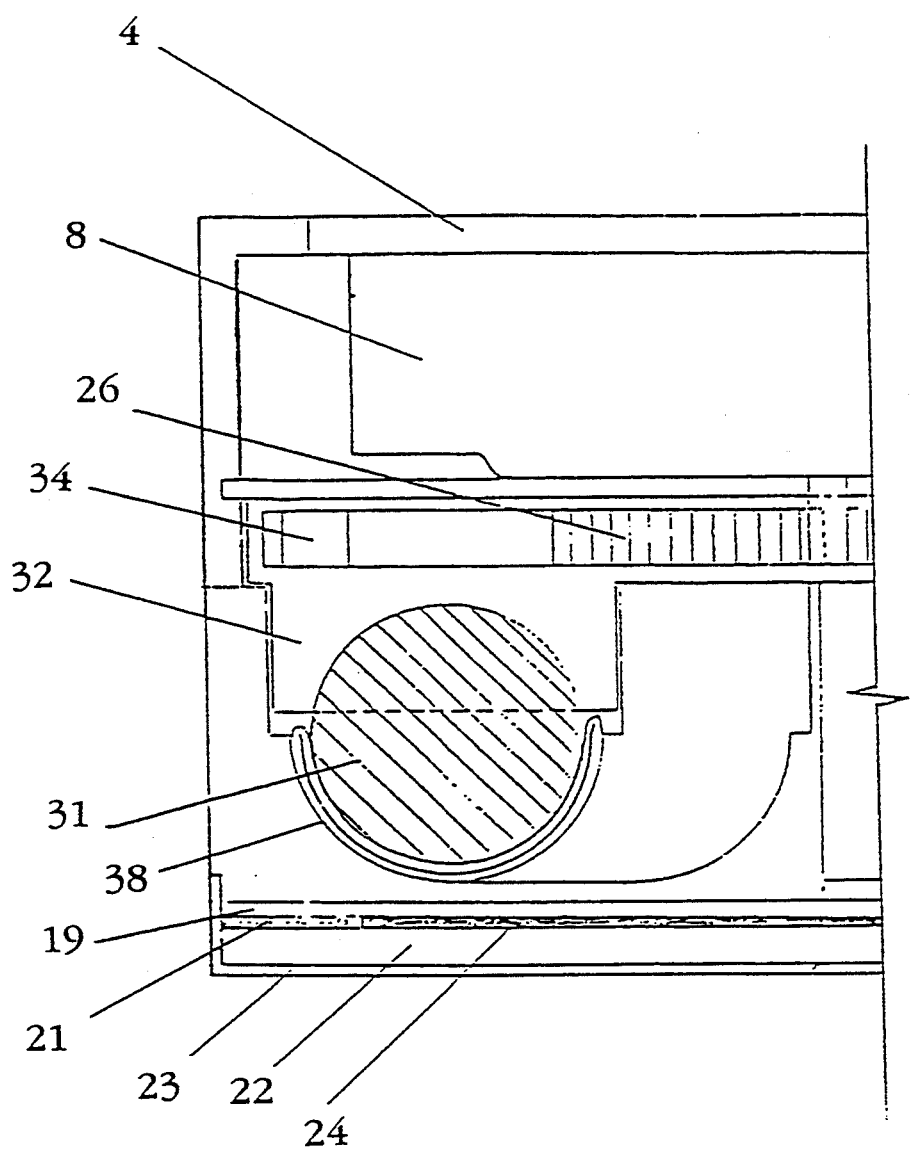
FIG. 9 is a cross-sectional view of the embodiment of FIG. 8, taken along the line IX—IX.

The third embodiment of the cartridge 2 is shown in an exploded view in FIG. 8. The peristaltic pump includes a hose-type pouch which replaces the collapsible medicament pouch 12 described above. The pouch 38 is placed in an arcuate chamber 12a and is filled with medicament 11. A ball 31 snugly fits in the arcuate chamber 12. The ball 31 serves to drive the medicament 11 before it as it is released through a release opening 30. FIG. 9 shows the pouch 38 in its collapsed form. The ball 31 is controllably driven by a drive mechanism including escapement wheel 34 controlled by an anchor 33 which is in turn operated by an electric solenoid 35. The escapement wheel 34 is spring biased by a coil spring 26 in direction shown by arrow A. For each operation of the anchor 33, the anchor wheel advances one step, driving before it, by means of an extension 32 on the underside of the escapement wheel, the ball 31. The medicament 11 released through release opening 30 is distributed through the elements 24, 21, 22 and 23 described above, and shown in FIG. 5c, namely the transducer 24, the annular sponge 21, transfer gel layer 22, and the interface membrane 23.

Alternatively, from the element 29, the medicament may travel to the center where a release opening is disposed. In that embodiment the layer 24 is a capillary chamber or a sponge to radially distribute the medicament toward the sponge 21 and the element 22 then in the transducer.

The solenoid 35 is operated by electric pulses generated by a control circuitry including a pulse generator and timing circuits which operate to dispense the medicament 11 as required and regulated by instructions stored in an EEPROM, described in more detail below.

FIG. 9 shows the invention composed of the elements of FIG. 8 in assembled form, wherein same reference numerals indicate same elements.

A wide array of experiments have been conducted by the inventors. Two exemplary results are shown in FIGS. 10 and 11a–11d. Insulin levels of a hairless mouse (animal #85) are shown as a function of patch on-off time in FIG. 10. As clearly shown by the curve, insulin levels are drastically increased during the periods when the device is on.

Figure 11A:
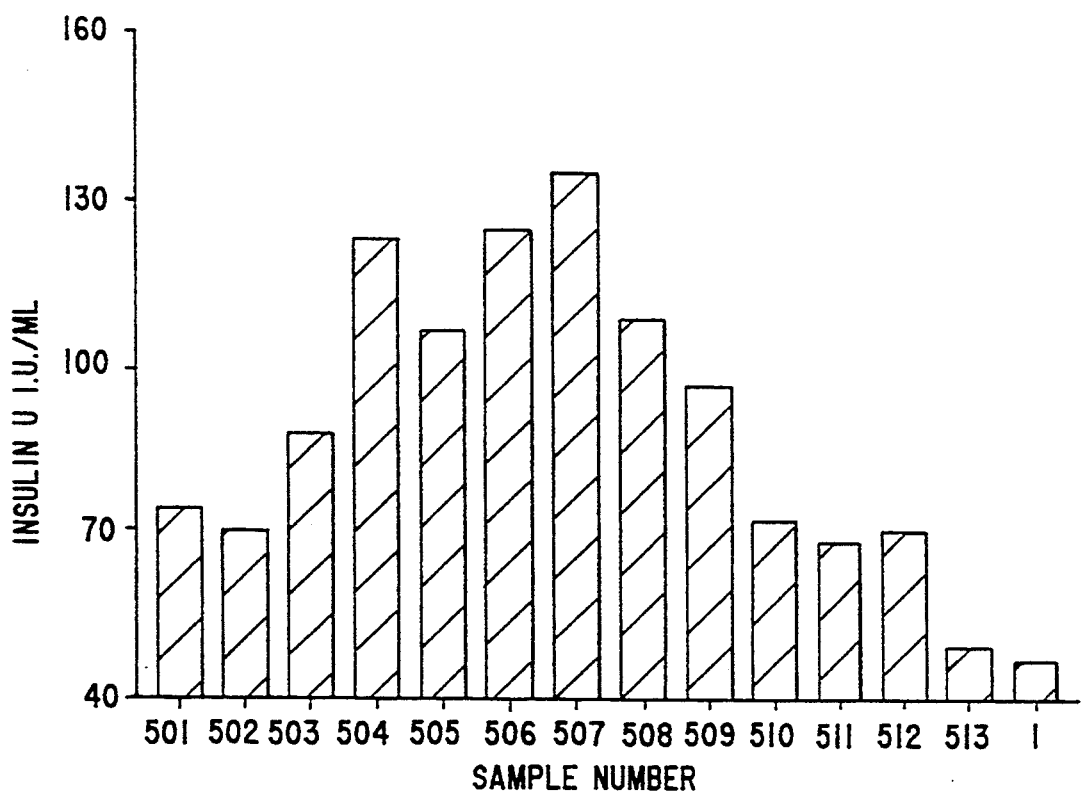
FIGS. 11a-11d are diagrams of exemplary human test results.
Figure 11C:
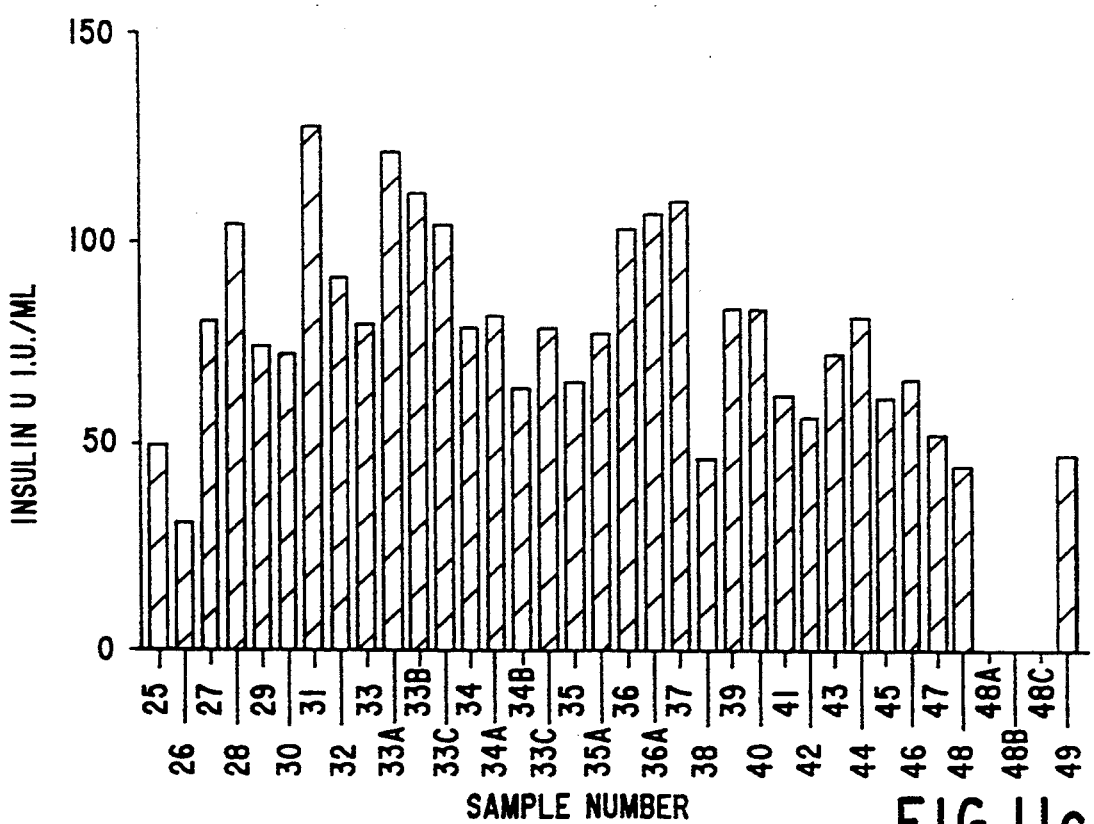
Figure 11B:
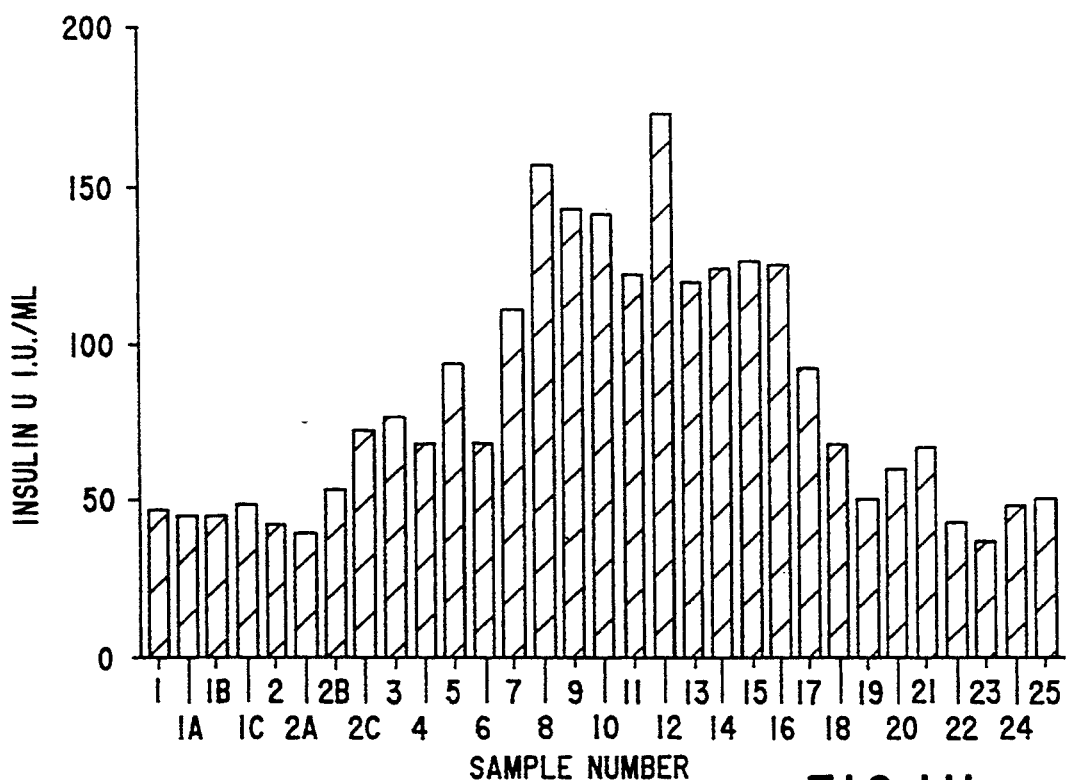
Figure 11D:
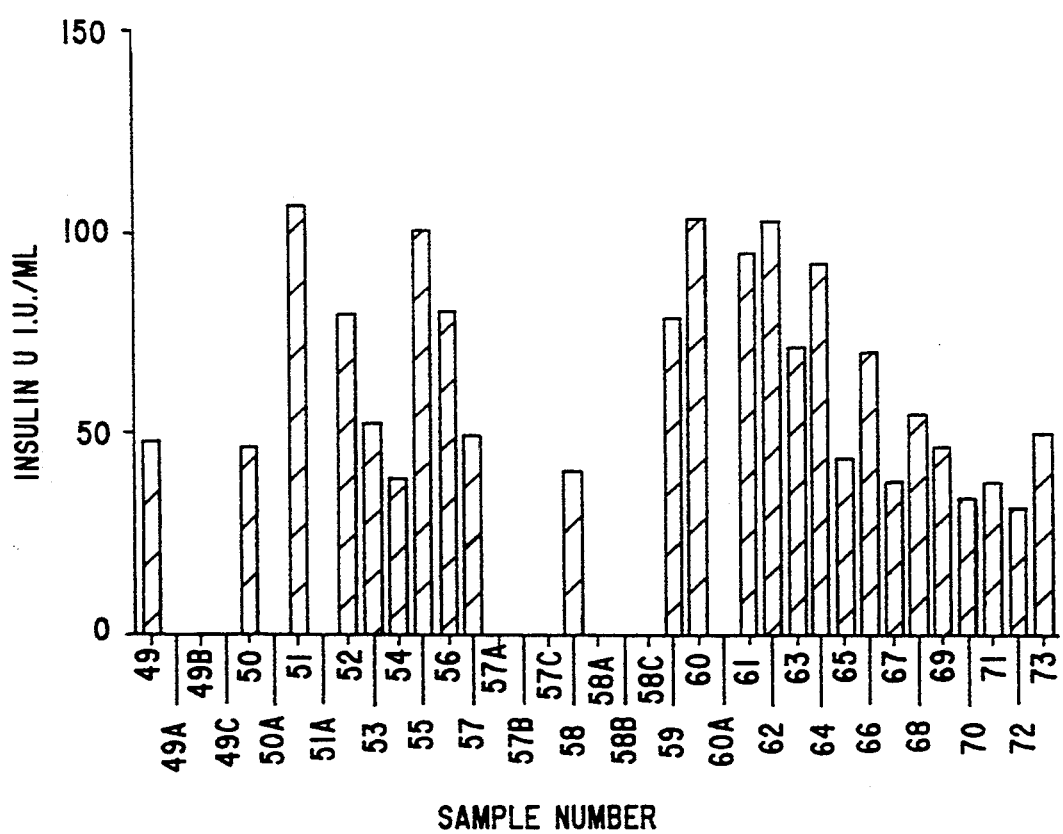

The human testing results (patient #6) show extremely good response as well. FIG. 11a shows that patient's typical curve after an injection at time 500. Samples were taken every hour. The sample measurements of FIGS. 11b–11d were taken at 15-minute intervals. The openings in the bar graph diagrams of FIGS. 11c and 11d mean that no samples were taken during those periods.

While the various embodiments described and shown herein pertain to a watch-like wrist band, the invention is nevertheless not limited to that embodiment. A band around any body part is also envisioned. Furthermore, the devices are being tested with a remote timing unit, i.e. the dispensing and timing units are disposed remote from one another. In that context, the dispensing cartridge may be used as a skin patch whose dispensing of medicament is controlled by a remote electronic unit.

Furthermore, in the case of insulin administration, the timing control of the electronic unit may be driven by a glucose sensor. Such sensors are commercially available and a person of skill in the art will be able, without undue experimentation, to provide a proper connection from the glucose sensor to the device according to the invention, such that the Basal dispensing of medicament is controlled by the sensor.

Figure 12:
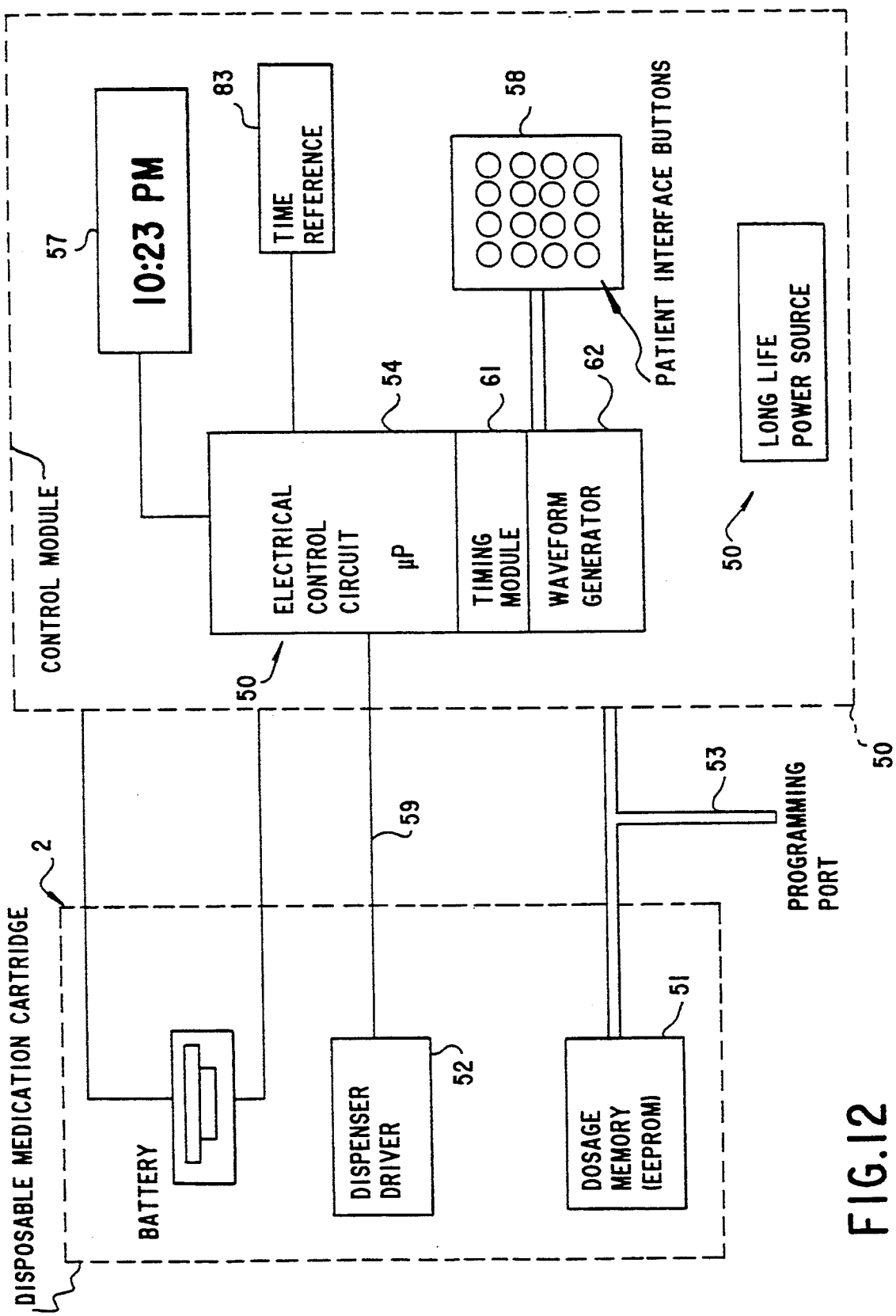
FIG. 12 is a block diagram of the main block of a cartridge.

FIG. 12 is a block diagram of the main block of the disposable medication cartridge 2, shown in a dotted line box, and connected with a control module 50, which serves to generate control signals for a dispenser driver 52, in response to timing instructions stored in an EEPROM 51.

A programming port 53 is provided for inserting timing instructions into the EEPROM 51 from an external programming device.

The control module 50 includes a control circuit 54, for example a microcomputer 54, or other programmable control device. The control circuit 54 is driven by a time reference 83 which supplies basic clock pulses driving the control circuit 54 with a timing module 61, which drives a waveform generator 62 and a clock display 57. The control circuit 54 is connected with a patient interface button set 58 which serves to manually enter timing instructions into the EEPROM 51 via the control circuit 54. The control circuit 54 provides drive signals for the dispenser driver 52 via electrical connections which are realized by the contact set 7a in FIG. 1.

Figure 13:
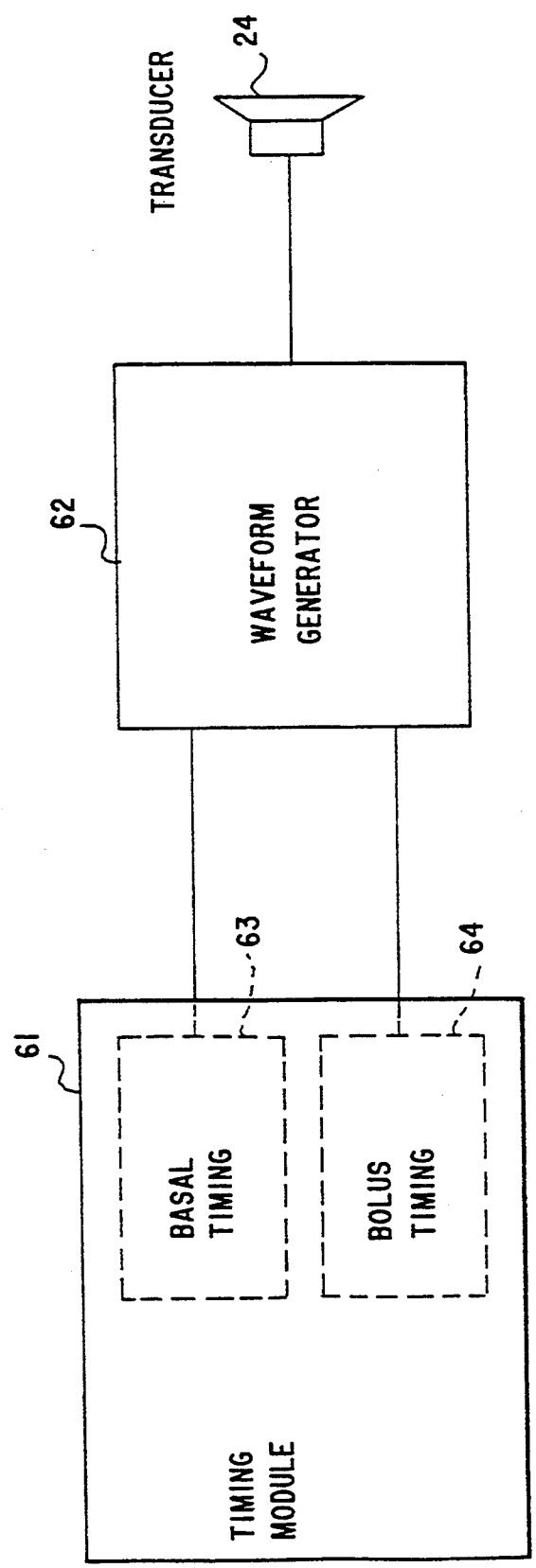
FIG. 13 is a block diagram of a control circuit.

FIG. 13 shows parts of the control circuit 54, including the timing module 61, composed of a basal timing part 63, providing continuous timing for the flow control device, and a time-limited bolus timing part 64, which overrides the basal timing, and can be activated by the patient by operating the bolus timing key 42 (FIG. 2). The bolus timing overrides the basal timing whenever a drug dispensing program different from the basal timing is desired by the patient. A waveform generator 62 provides the particular optimal signal waveform used to drive the transducer 24.

Figure 14:
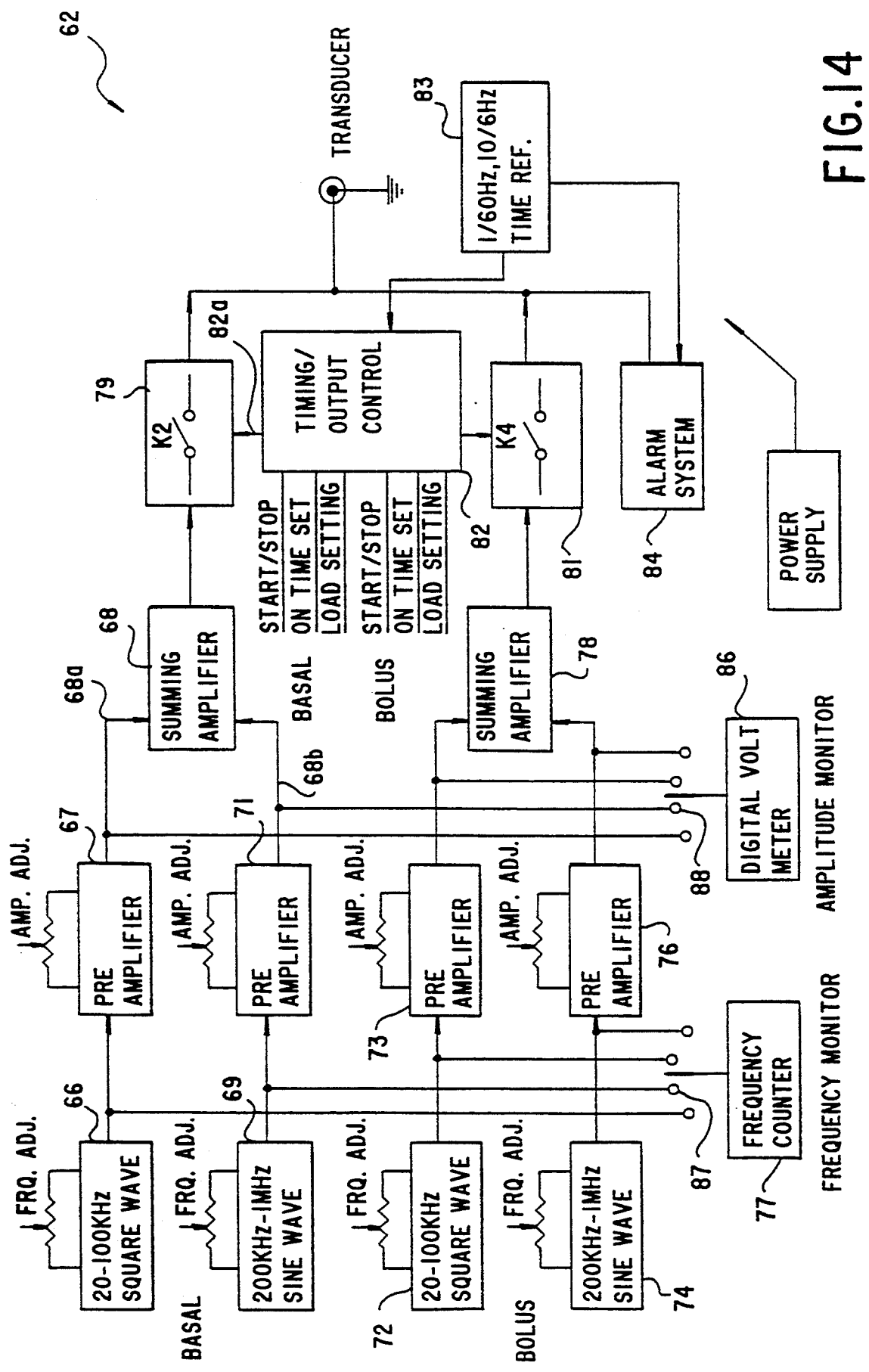
FIG. 14 is a block diagram of a waveform generator according to the invention.

FIG. 14 shows the waveform generator 62 in block diagram form, wherein an adjustable square wave generator 66 with frequency range 20–100 KHz produces a square wave input to an adjustable pre-amplifier 67, which produces an amplified square wave input 68a to a summing amplifier 68. An adjustable sine wave generator 69 with a frequency range from 200 KHz to 1 MHz produces a sine wave input to an adjustable pre-amplifier 71, producing an amplified sine-wave input 68b to the summing amplifier 68. The summing amplifier 68 produces a basal timing input signal of the superimposed 20–100 KHz square wave and the 200 KHz–1 MHz sine wave to the transducer 24 via a time-controlled switch 79 (K2), controlled by a timing/output control circuit 82.

The bolus signal wave form is generated by similar circuits which include an adjustable square wave generator 72 driving an adjustable pre-amplifier 73 connected to a summing amplifier 78, and an adjustable sine-wave generator 74 connected to an adjustable pre-amplifier 76, connected to another input of the summing amplifier 78, connected to another time-controlled switch 81 (K4), also controlled by timing/output control 82, which provides the bolus signal for the transducer 24.

A timing/output control 82 provides respective start and stop signals for the switches 79 and 81.

FIG. 15 shows the timing pulses that are generated by the timing module 61, and which control the timing of the administration of the medicament.

In FIG. 15, line "a" shows the start pulse 101 that initiates a cycle of "on" states 102 (line "b") in the basal mode. In the "on" state, the switch K2 in FIG. 14 is turned on, which starts application of the ultrasonic wave signal to the transducer 24, and simultaneously activates the valve 44 in FIG. 5b so that administration of the medicament is performed in the "on" states 102, shown in line "b". The "on" state is applied for a duration ranging from 1 to 60 minutes beginning each hour as shown in FIG. 15, line "c" as hour pulses 103. The duration of the "on" state 102 is controlled by a timing circuit controlled e.g. by instructions stored in the EEPROM 51 (FIG. 12). The administration of a basal cycle of "on" states, each beginning each hour with hour pulse 103, is terminated by a "stop" pulse 104, as shown in line "a" after the basal cycle of a given number of "on" states have been administered, as also controlled by the instructions stored in the EEPROM 51.

In case the patient desires to alter the administration of medicament, e.g. to increase the amount being administered, or to reduce it, he activates the BOLUS knob or key 42 (FIG. 1), which causes the basal cycle to be interrupted and a bolus cycle of administrations to begin, as shown by the vertical dotted line 106, which indicates interruption of the basal cycle and beginning of a bolus cycle of "on" states 107, as shown in line "e". The duration of each bolus "on" state 107 is again controlled by instructions stored in the EEPROM 51. The bolus cycle is started by a bolus "start" pulse and is terminated by a bolus "stop" pulse 109. The bolus "on" state activates switch K4 in FIG. 14, and activation of the ultrasonic transducer 24. After the end of the bolus cycle at stop pulse 109, the basal cycle may be resumed, as it is programmed by the EEPROM to continue beyond the bolus cycle. The bolus "on" states are controlled by bolus hour pulses 111, as shown in line f.

FIG. 15, line g shows the waveform of the signal generated by the waveform generator (FIG. 14) as it is being applied to the ultrasonic transducer 24. The waveform is a superposition of a sine wave as generated by the pre-amplifiers 71, 76 (FIG. 14) and a square wave generated by respective pre-amplifiers 67, 73 (FIG. 14). The superposition of the two signals (sine wave and square wave) is performed linearly in the summing amplifiers 68, 78. The resulting superimposition of sine and square wave signal wave form has been found by clinical tests to be an important factor in enabling the transdermal transfer of medicaments.

Figures 15G, 16A:
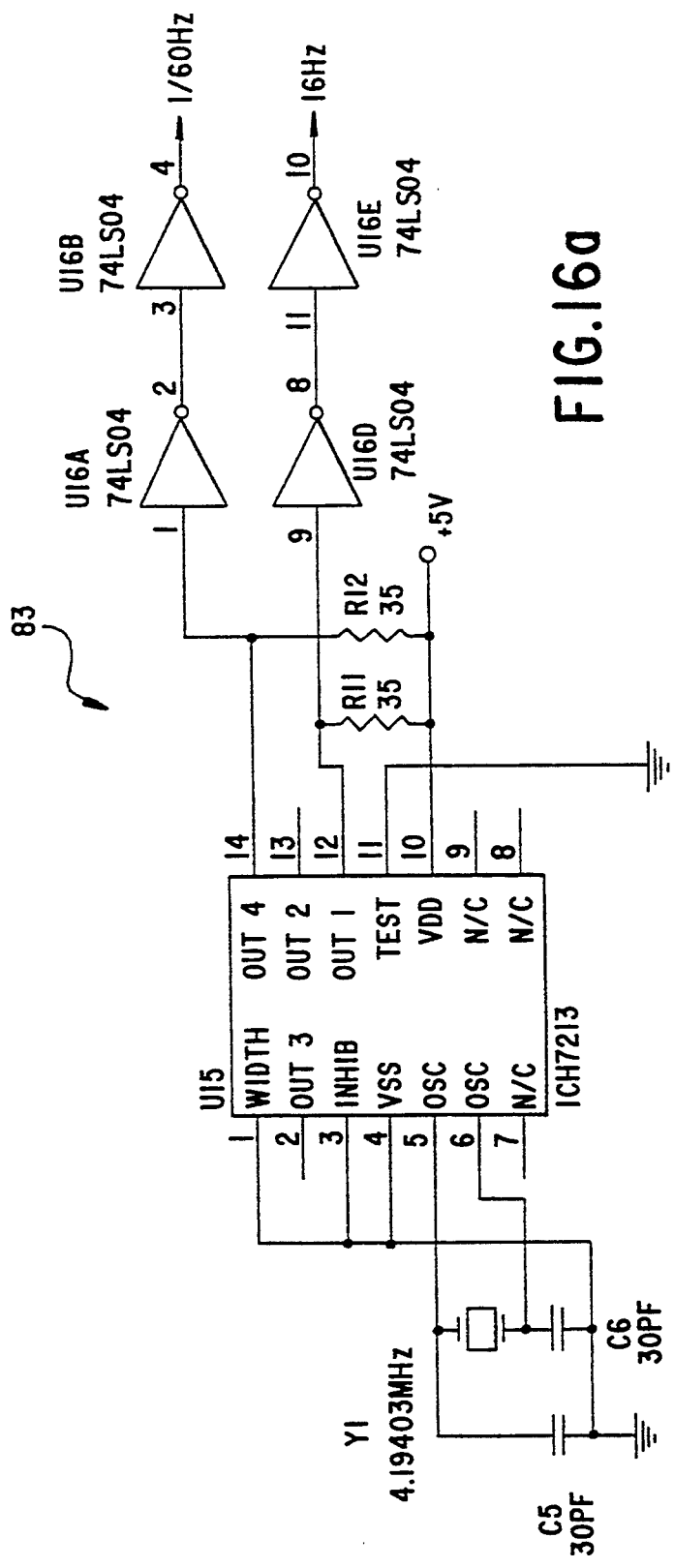
FIG. 16a is a view of a basic time reference circuit diagram.

With reference to FIG. 16a, a basic time reference 83 provides time reference signals to timing/output control 82, which in turn provides start-stop signals for the switches 79, 84. The switches are advantageously latching electronic gates controlled by the start-stop signals.

Figure 16B:
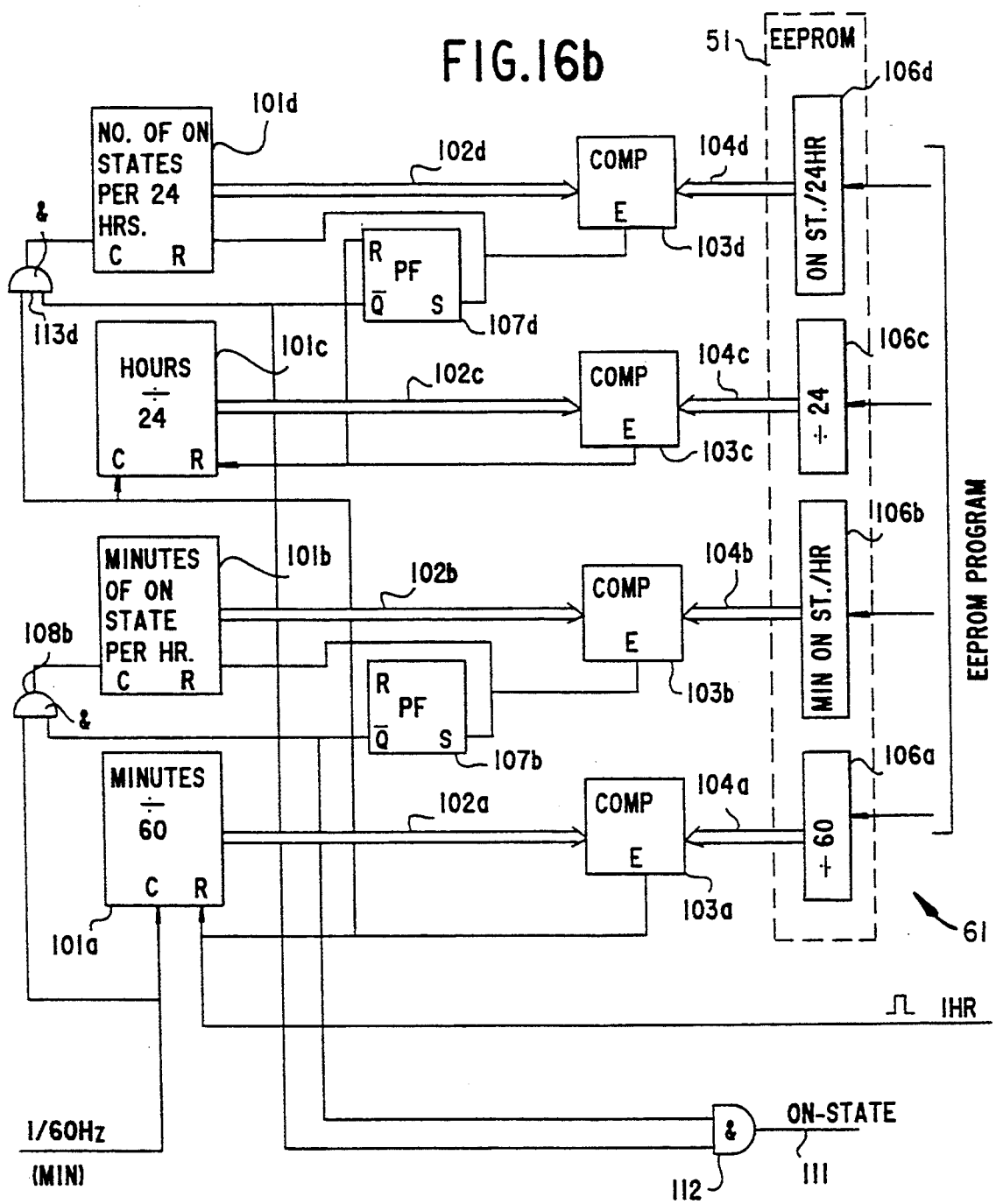
FIG. 16b is a diagrammatic view of a basic timing circuit.

FIG. 16b is a simplified block diagram of the timing module 61 (FIG. 12) in an embodiment that generates the on-state waveform for either the basal or the bolus timing in response to instructions programmed into the EEPROM 51. The timing circuit is composed of four cascaded ripple counters 101a, 101b, 101c and 101d driven by a 1/60 Hz, i.e. a one pulse per minute signal, from a time reference 83. Each counter has a respective output 102a–102d that represents a multibit output for each bit in the counter. Each counter is connected to one side of a respective comparator 103a–103d, while the other side of the counter is connected via multibit connections 104a–104d to a respective multibit word 106a–106d in the EEPROM 51. Each counter 101a–101d has a counting input C and a reset input R. Each counter reset input R is connected to an output E of a respective comparator, so that when a counter reaches a count equal to the word programmed to the EEPROM, the counters stops, and is reset and at the same time activates a subsequent one of the other counters.

In that manner the timing circuit can be programmed to generate an output control signal of any wave form determined by information programmed into the EEPROM.

Figure 16C:
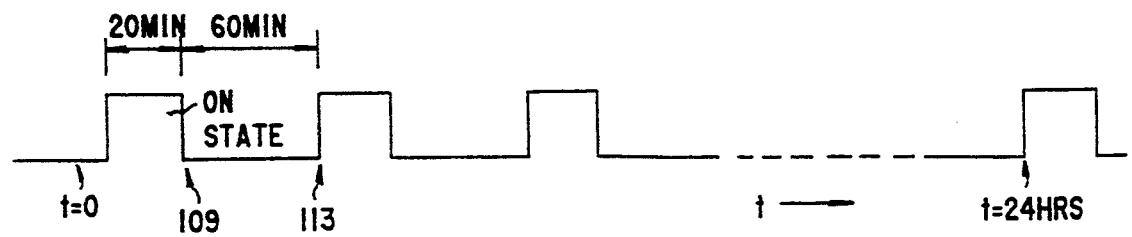
FIG. 16c is an exemplary pulse distribution diagram.

For the purpose of facilitating the following description of the operation of the timing module, it is presumed that the timing cycle is based on a one minute input (1/60 Hz) which is divided by 60 in the 101a counter, which thereby generates a pulse each hour on lead 1 HR. The duration of the on-state waveform is determined in counter 101b, which counts minute pulses until it reaches the count programmed into EEPROM section 106b. If the on-state condition is to be for example 20 minutes, a value equal to 20 is programmed into EEPROM section 106b. After "start" at time t equal to 0 in FIG. 16c, when counter 101b reaches a count equal to 20, a logic "1" appears on output E of comparator 103b which sets a flip-flop 107b at its input pin S. The inverted output $\bar{Q}$ inhibits the output of an AND-gate 108b driven by the minute input 1/60+12, and counter 101b stops counting, terminating the on-state output shown at point 109 in FIG. 16c. Counter 101a continues to count to the count of 60 at which time a pulse is generated at output E of comparator 103a, which resets minute counter 101a at input R, and also resets flip-flop 107b at input R.

The output $\bar{Q}$ of flip-flop 107b is gated out as a logic "high" on lead "ON-state" via AND-gate 112, already enabled at its lower input by flip-flop 107d, which is at this time in its reset condition. When flip-flop 107b is reset after 20 minute pulses are received, the ON-state on lead 111 goes back to logic "low", terminating the ON-state pulse at time 109 in FIG. 16c. After 60 minutes from start 109, the hour counter 101c receives the first hour pulse at input C from comparator 103a and starts counting one hour for each 60 minutes that have elapsed, until 24 hours have been counted in counter 101c, at which time flip-flop 101d is reset at its input R which enables AND-gate 113d as its output $\bar{Q}$ goes high. The AND-gate 113d is at the same time enabled by the 1 hour pulse from the output E of comparator 103a and advances the "number of ON-states per 24 hours" counter 101d by one count.

Counting proceeds until a number of hour counts corresponding to the number stored in EEPROM 106d is reached by hour counter 101d. In the example shown in FIG. 16c three ON-state pulses, will be counted, presuming that a number equal to three is stored in EEPROM section 106d, after which a new 24-hour cycle is repeated, again measuring 3 one-hour ON-state pulses, which is the continuously running basal time waveform.

It follows that the waveform can be controlled in all parameters with an accuracy of one minute, according to information programmed into the EEPROM 51. It also follows that the timing need not be based on 60 minute hours or 24 hour cycles, since the hour and minute counters are also programmed into the EEPROM 51.

The bolus timing is performed by a similar counter which can be connected to EEPROM 51, or to another EEPROM if the bolus timing is desired to be different. The bolus timing can be based on the same 1/60 Hz, i.e. one pulseper minute, driving the basal timing counter, but will during bolus timing be gated to generate its corresponding output wave form in response to operation of the BOLUS key 42 (FIG. 1), which is arranged to override the basal waveform shown in FIGS. 16c and 15, lines D and E. The bolus timing can advantageously be arranged to measure out only a single cycle of ON-states, by providing a counter control flip-flop (not shown) that is set only once by the BOLUS key 42, and is automatically reset as the last, for example, one of three hour ON-states, have elapsed.

An alarm system 84 monitors the output signals from switches 79, 81 and generates an audible alarm in case failures in the signal to the transducer 24 are detected.

Monitor connections 87, 88 can be provided for connection to a respective external frequency counter 77 and voltmeter 86.

FIG. 17 shows circuit details of the waveform generator 62. FIG. 17 applies to both the basal and the bolus sections 63, 64, respectively, of waveform generator 62 shown in FIG. 13.

FIG. 17, section a shows circuit details of the waveform generator 62, as they apply to both the basal and the bolus section. Reference numerals 66, 72 show a variable voltage circuit block formed of a voltage control circuit 89 controlling the frequency of a square wave generator 91, e.g. a conventional astable type 555 timer driving an adjustable op-amp 92, connected via diode 93 and resistor 94 to the inverting input of summing amplifiers 68, 78.

FIG. 17, section c shows in the dashed line box 69, 74 a sine wave generator formed of a voltage control circuit 96 driving a triangle-wave circuit 97 again, e.g. an astable type 555 timer, connected to an active low-pass filter 98, which in turn converts the triangle wave to a sine wave and drives adjustable amplifier 99 with a sine wave input. Amplifier 99 provides the sine wave input to summing amplifiers 68, 78 via resistors 94, 101, respectively.

FIG. 17, section b shows a power supply 8a of conventional construction, which supplies the various voltages V1, V2, V3, as required by the electrical circuits of the transdermal drug delivery device. Battery 8 supplies the required input power to the power supply 8a.

It is claimed:

1. An assembly for the transdermal administration of a drug to a patient, comprising:
   a base unit having a timer and electrical connections for issuing electronic timing information from said timer; a drug administration unit electrically connected to said base unit, said drug administration unit having a housing defining a space therein for receiving a drug and said housing having drug dispensing conduit means formed therein, a skin-contacting surface to be placed on a patient's skin, dispensing means for selectively causing time-dependent dispensing of a drug from said space in said housing through said conduit means to said skin-contacting surface and to the patient's skin, and means for generating pressure waves at said skin contacting surface for facilitating transdermal absorption of the drug dispensed to said skin contacting surface.

2. The assembly according to claim 1, wherein said dispensing means comprises valve means disposed in said conduit means for selectively closing and opening said conduit means.

3. The assembly according to claim 1, wherein said pressure wave generating means comprise a transducer disposed at said skin contacting surface, and circuit means operatively connected to said transducer for driving said transducer at a given frequency.

4. The assembly according to claim 3, wherein said circuit means comprises wave form generator means for generating an electronic signal formed of a square wave in a frequency range of between 20 KHz and 100 KHz and of a sine wave superimposed thereon in a frequency range of between 200 KHz and 1 MHz.

5. The assembly according to claim 1, wherein said pressure waves generating means include an ultrasonic transducer for generating ultrasonic waves aimed at the patient's skin and an ultrasonic waveform generator drivingly connected to said transducer.

6. The assembly according to claim 1, including in said conduit means a skin area interface membrane for contacting the skin area, a layer of transfer gel in contact with said interface membrane, an open cell foam body having one side connected with said transfer gel, a medicament distribution chamber communicating at one side with said foam body and at an opposite side with said flow means.

7. The assembly according to claim 1, wherein said transducer is a planar piezo-electric disc electrically connected with said ultrasonic waveform generator.

8. The assembly according to claim 5, including in said ultrasonic waveform generator at least one sine wave generator, at least one square wave generator, a summing circuit having respective inputs connected to said sine wave generator and to said square wave generator for generating a superimposed signal of said sine wave and said square wave connected to said transducer.

9. The assembly according to claim 8, wherein said timing circuit is operative for activating said waveform generator in alternating on and off states in programmed sequence.

10. The assembly according to claim 9, including in said timing circuit EEPROM means for storing at least one timing program for timing said programmed sequence.

11. The assembly according to claim 10, including stored in said EEPROM means at least one basal timing sequence and at least one bolus timing sequence.

12. The assembly according to claim 11, including on said housing a plurality of control knobs connected to said electrical control circuit, wherein one of said control knobs is operative for activating said basal timing sequence, and a second one of said control knobs is operative for activating said bolus timing sequence.

13. The assembly according to claim 12, wherein said bolus sequence overrides said basal timing sequence.

14. The assembly according to claim 13, wherein said bolus timing sequence is time-limited.

15. The assembly according to claim 10, including an access port connected to said EEPROM means, said access port operative for accessing external programming means for entering timing programs into said EEPROM.

16. The assembly according to claim 1, including in said base unit an alarm system for generating an alarm in case of failure of said timer.

17. The assembly according to claim 16, including an audible alarm transmitter connected to said alarm system for generating an audible alarm in case of failure of said timer.

* * * * *